US011279954B2

(12) United States Patent
Mitrophanous et al.

(10) Patent No.: US 11,279,954 B2
(45) Date of Patent: Mar. 22, 2022

(54) CATECHOLAMINE ENZYME FUSIONS

(71) Applicant: Oxford BioMedica (UK) Ltd., Oxford (GB)

(72) Inventors: Kyriacos A. Mitrophanous, Oxford (GB); Scott Ralph, Oxford (GB); Hannah Stewart, Oxford (GB); Alan John Kingsman, Oxford (GB)

(73) Assignee: Oxford BioMedica (UK) Ltd., Oxford (GB)

( * ) Notice: Subject to any disclaimer, the term of this patent is extended or adjusted under 35 U.S.C. 154(b) by 51 days.

(21) Appl. No.: 16/454,024

(22) Filed: Jun. 26, 2019

(65) Prior Publication Data

US 2020/0040361 A1 Feb. 6, 2020

Related U.S. Application Data

(62) Division of application No. 13/661,618, filed on Oct. 26, 2012, now Pat. No. 10,400,252.

(60) Provisional application No. 61/552,581, filed on Oct. 28, 2011.

(51) Int. Cl.

| | |
|---|---|
| ***A61K 48/00*** | (2006.01) |
| ***C12N 15/867*** | (2006.01) |
| ***A61K 38/54*** | (2006.01) |
| ***C12N 9/02*** | (2006.01) |
| ***C12N 9/78*** | (2006.01) |
| ***C12N 9/88*** | (2006.01) |

(52) U.S. Cl.

CPC ............ *C12N 15/867* (2013.01); *A61K 38/54* (2013.01); *A61K 48/00* (2013.01); *A61K 48/005* (2013.01); *C12N 9/0071* (2013.01); *C12N 9/78* (2013.01); *C12N 9/88* (2013.01); *C07K 2319/00* (2013.01); *C12N 2740/15043* (2013.01); *C12N 2830/48* (2013.01); *C12N 2840/203* (2013.01)

(58) Field of Classification Search

CPC ...... C12N 15/867; C12N 9/0071; C12N 9/78; C12N 9/88; C12N 2740/15043; C12N 2830/48; C12N 2840/203; A61K 48/005; A61K 48/00; A61K 38/54; C07K 2319/00

See application file for complete search history.

(56) References Cited

U.S. PATENT DOCUMENTS 9,339,512 B2 * 5/2016 Widdowson ............ A61P 25/08
2004/0013648 A1 * 1/2004 Kingsman ............... A61P 25/16 424/93.2

FOREIGN PATENT DOCUMENTS

WO WO9718319 A1 5/1997
WO WO9818934 5/1998
WO WO-9818934 A1 * 5/1998 ........... C12N 9/0071
WO WO2002029065 4/2002
WO WO2010055290 A1 7/2004

OTHER PUBLICATIONS

Jarraya et al Science Transl Med. 1(2) , 1-11 (Year: 2009).*
Axelsen et al Journal of Parkinson's Disease 8, 195-215 (Year: 2018).*
Azzouz et al., J. Neurosci., vol. 22(23), p. 10302-10312 (Year: 2002).*
Chen et al. (Current Gene Therapy, vol. 5, 71-80 (Year: 2005).*
Olguin et al Oxidative Medicine and Cellular Longevity vol. 1-13 (Year: 2016).*
Soudais, et al FASEB J., 18(2): 391-3 (Year: 2004).*
Kuhn D M et al., "Tetrahydrobiopterin prevents nitration of tyrosine hydroxylase by peroxynitrite and nitrogen dioxide", Molecular pharmacology, 2003, vol. 64, No. 4 pp. 946-953.
Wu et al., A novel therapeutic approach to 6-OHDA-induced Parkinson's Disease in Rats via Supplementation . . . , Biochem Biophys Res Comm, 2006, vol. 346, No. 1 pp. 1-6.
Azzouz et al., 2002 J Neurosci 2002, vol. 22, No. 23, pp. 10302-10312.
Bowling et al , Journal of Biological Chemistry, 282, 31449-31459.
Wu D and Cepko C L, The Stability of Endogenous Tyrosine Hydroxylase Protein in PC-12 Cells . . . , Journal of Neurochemistry, vopl 62, No. 3, pp. 863-872.
Schöffski P, Polo-Like Kinase (PLK) Inhibitors in Preclinical and Early Clinical Development in Oncology, The Oncologist, 2009, vol. 14, pp. 559-570.
Degenhardt Y and Lampkin T, Targeting Polo-like Kinase in Cancer Therapy, Clinical Cancer Research, Jan. 15, 2010, vol. 16(2) pp. 384-389.
Jarvis L M, PI3K at the Clinical Crossroads, Chemical & Engineering News, Apr. 11, 2011, vol. 89, No. 15, pp. 15-19.
Holmes D, PI3K pathway inhibitors approach junction, Nature Reviews Drug Discovery, Aug. 2011, vol. 10, pp. 563-564.
Engelman J A, Targeting PI3K signalling in cancer: opportunities, challenges and limitations, Nature, Aug. 2009, vol. 9, pp. 550-562.
Steegmaier M et al., BI 2536, a Potent and Selective Inhibitor of Polo-like Kinase 1, Inhibits Tumor Growth In Vivo, Current Biology, Feb. 20, 2007, vol. 17, pp. 316-322.

(Continued)

*Primary Examiner* — Anoop K Singh
(74) *Attorney, Agent, or Firm* — Grimes & Yvon LLP

(57) ABSTRACT

Provided is a construct comprising (i) a nucleotide sequence which encodes tyrosine hydroxylase (TH), (ii) a nucleotide sequence which encodes GTP-cyclohydrolase I (CH1) and (iii) a nucleotide sequence which encodes Aromatic Amino Acid Dopa Decarboxylase (AADC) wherein the nucleotide sequence encoding TH is linked to the nucleotide sequence encoding CH1 such that they encode a fusion protein TH-CH1. Also provided is a construct comprising (i) a nucleotide sequence which encodes tyrosine hydroxylase (TH), (ii) a nucleotide sequence which encodes GTP-cyclohydrolase I (CH1) and (iii) a nucleotide sequence which encodes Aromatic Amino Acid Dopa Decarboxylase (AADC) wherein the nucleotide sequence encoding AADC is linked to the nucleotide sequence encoding TH such that they encode a fusion protein AADC-TH or TH-AADC. Further provided is a viral vector comprising such nucleotide sequences and its use in the treatment and/or prevention of Parkinson's disease.

4 Claims, 18 Drawing Sheets

Specification includes a Sequence Listing.

(56) References Cited

OTHER PUBLICATIONS

Jamieson S et al., A drug targeting only p110α can block phosphoinositide 3-kinase signalling and tumour growth in certain cell types, Biochem J, 2011, vol. 438, pp. 53-62.
Engelman J A et al., The evolution of phosphatidylinositol 3-kinases as regulators of growth and metabolism, Nature, Aug. 2006, vol. 7, pp. 606-619.
Zhao and Vogt, Class I PI3K in oncogenic cellular transformation, Oncogene, 2008, vol. 27, pp. 5486-5496.

* cited by examiner

2a

2b

3a

3b

*Expected Protein Sizes:*

| | kDa | | | | | |
|---|---|---|---|---|---|---|
| **EIAV genome** | **TH** | | **CH1** | | **AADC** | |
| pONYK1 (standard) | 42 | ✓ | 26 | ✓ | 26 | ✓ |
| pONYK-TAiC | 98 | ✓ | 26 | ✓ | 26 | ✓ |
| pONYK-ATiC | 98 | ✓ | 26 | ✓ | 26 | ✓ |
| pONYK-TCiA | 68 | ✓ | 68 | ✓ | 68 | ✓ |
| pONYK-ATC | 124 | ✓ | 124 | ✓ | 124 | ✓ |

6a TH Western Blot Analysis

*Expected TH Protein Sizes*

| EIAV genome | kDa | Result |
|---|---|---|
| pONYK1 | 42 | ✓ |
| pONYK-ATiC | 98 | ✓ |
| pONYK-TAiC | 98 | ✓ |
| pONYK-TCiA | 68 | ✓ |
| pONYK-CTiA | 68 | ✓ |
| pONYK-AiTC | 68 | |
| pONYK-ATC | 124 | ✓ |
| pONYK-TCA | 124 | ✓ |
| pONYK-ATCmod | 124 | ✓ |
| pONYK-TCAmod | 124 | ✓ |

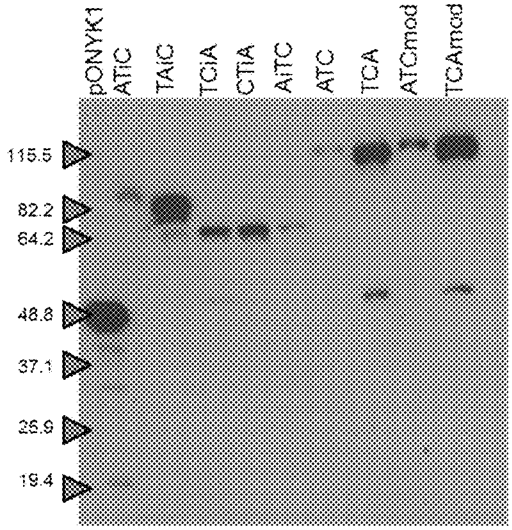

6b CH1 Western Blot Analysis

*Expected CH1 Protein Sizes*

| EIAV genome | kDa | Result |
|---|---|---|
| pONYK1 | 26 | ✓ |
| pONYK-ATiC | 26 | ✓ |
| pONYK-TAiC | 26 | ✓ |
| pONYK-TCiA | 68 | ✓ |
| pONYK-CTiA | 68 | ✓ |
| pONYK-AiTC | 68 | ✓ |
| pONYK-ATC | 124 | ✓ |
| pONYK-TCA | 124 | ✓ |
| pONYK-ATCmod | 124 | ✓ |
| pONYK-TCAmod | 124 | ✓ |

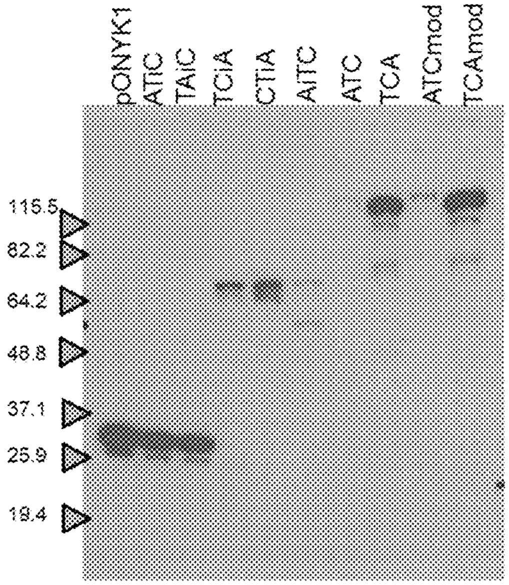

6c AADC Western Blot Analysis

*Expected AADC Protein Sizes*

| **EIAV genome** | **kDa** | **Result** |
|---|---|---|
| pONYK1 | 56 | ✓ |
| pONYK-ATiC | 98 | ✓ |
| pONYK-TAiC | 98 | ✓ |
| pONYK-TCiA | 56 | ✓ |
| pONYK-CTiA | 56 | ✓ |
| pONYK-AiTC | 56 | ✓ |
| pONYK-ATC | 124 | ✓ |
| pONYK-TCA | 124 | ✓ |
| pONYK-ATCmod | 124 | ✓ |
| pONYK-TCAmod | 124 | ✓ |

8a *TH Western Blot Analysis*

| EIAV genome | Expected size (kDa) | Result |
|---|---|---|
| pONYK1 | 42 | ✓ |
| ATiC | 98 | ✓ |
| TAiC | 98 | ✓ |
| TCiA | 68 | ✓ |
| CTiA | 68 | ✓ |
| AiTC | 68 | ✓ |
| ATC | 124 | ✓very weak |
| TCA | 124 | ✓ |
| ATCmod | 124 | ✓ weak |
| TCAmod | 124 | ✓ |
| Untransduced (UTC) | N/A | ✓ |

8b *CH1 Western Blot Analysis*

| EIAV genome | Expected size (kDa) | Result |
|---|---|---|
| pONYK1 | 26 | |
| ATiC | 26 | |
| TAiC | 26 | |
| TCiA | 68 | ? * |
| CTiA | 68 | ? * |
| AiTC | 68* | ? * |
| ATC | 124 | ✓ weak |
| TCA | 124 | ✓ |
| ATCmod | 124 | ✓ weak |
| TCAmod | 124 | 124 |
| Untransduced (UTC) | N/A | ✓ |

8c *AADC Western Blot Analysis*

| EIAV genome | Expected size (kDa) | Result |
|---|---|---|
| pONYK1 | 56 | ✓ |
| ATiC | 98 | ✓ weak |
| TAiC | 98 | ✓ |
| TCiA | 56 | ✓ weak |
| CTiA | 56 | ✓ weak * |
| AiTC | 56 | ? * |
| ATC | 124 | x Not detected |
| TCA | 124 | ✓ |
| ATCmod | 124 | x Not detected |
| TCAmod | 124 | ✓ |
| Untransduced (UTC) | N/A | ✓ |

10a

10b

11a

11b

12a

EIAV-GFP MOI 2 EIAV-GFP MOI 10

12b

13a *TH Western Blot*

| Vector | Expected size (kDa) | Result |
|---|---|---|
| pONYK1 | 42 | ✓ |
| TCiAmod | 68 | ✓ |
| TCtkA | 68 | ✓ |
| TACmod | 124 | ✓ |
| GFP | N/A | |

13b *AADC Western Blot*

| Vector | Expected size (kDa) | Result |
|---|---|---|
| pONYK1 | 56 | ✓ |
| TCiAmod | 56 | ✓ |
| TCtkA | 56 | ✓ very weak |
| TACmod | 124 | ✓ |
| GFP | N/A | |

SEQUENCE LISTING

```
<160> NUMBER OF SEQ ID NOS: 10

<210> SEQ ID NO 1
<211> LENGTH: 45
<212> TYPE: DNA
<213> ORGANISM: Artificial Sequence
<220> FEATURE:
<223> OTHER INFORMATION: Description of Artificial Sequence: Synthetic
      linker-encoding oligonucleotide

<400> SEQUENCE: 1

ggaggtggcg ggtccggggg cgggggtagc ggtggcgggg gctcc                 45


<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 2

Gly Gly Gly Gly Ser Gly Gly Gly Gly Ser Gly Gly Gly Gly Ser
1               5                   10                  15


<210> SEQ ID NO 3
<211> LENGTH: 45
<212> TYPE: DNA
<213> ORGANISM: Artificial Sequence
<220> FEATURE:
<223> OTHER INFORMATION: Description of Artificial Sequence: Synthetic
      linker-encoding oligonucleotide

<400> SEQUENCE: 3

gggggaggcg gtagcggcgg agggggctcc ggcggaggcg ggagc                 45
```

-continued

```
<210> SEQ ID NO 4
<211> LENGTH: 25
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 4

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25


<210> SEQ ID NO 5
<211> LENGTH: 21
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 5

Asn Phe Ile Arg Gly Arg Glu Asp Leu Leu Glu Lys Ile Ile Arg Gln
1               5                   10                  15

Lys Gly Ser Ser Asn
            20


<210> SEQ ID NO 6
<211> LENGTH: 23
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 6

Asn Leu Ser Ser Asp Ser Ser Leu Ser Ser Pro Ser Ala Leu Asn Ser
1               5                   10                  15

Pro Gly Ile Glu Gly Leu Ser
            20


<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 7

Gln Gly Ala Thr Phe Ala Leu Arg Gly Asp Asn Pro Gln Gly
1               5                   10


<210> SEQ ID NO 8
<211> LENGTH: 18
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 8

Ser Gly Gly Gly Glu Ile Leu Asp Val Pro Ser Thr Gly Gly Ser Ser
1               5                   10                  15

Pro Gly
```

-continued

```
<210> SEQ ID NO 9
<211> LENGTH: 148
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Truncated TH linked to AADC via a GS15 linker

<400> SEQUENCE: 9

ggcgctccct ggagggtgtc caggatgagc tggacaccct tgcccatgcg ctgagcgcca     60

tcggcggggg aggcggtagc ggcggagggg gctccggcgg aggcgggagc atggacgcca    120

gtgagttccg aaggcgcggc aaggagat                                       148


<210> SEQ ID NO 10
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Truncated TH linked to AADC via a GS15 linker

<400> SEQUENCE: 10

Arg Arg Ser Leu Glu Gly Val Gln Asp Glu Leu Asp Thr Leu Ala His
1               5                   10                  15

Ala Leu Ser Ala Ile Gly Gly Gly Gly Gly Ser Gly Gly Gly Gly Ser
            20                  25                  30

Gly Gly Gly Gly Ser Met Asp Ala Ser Glu Phe Arg Arg Arg Gly Lys
        35                  40                  45

Glu Met
    50
```

CATECHOLAMINE ENZYME FUSIONS

CROSS-REFERENCE TO RELATED APPLICATIONS

This application is a divisional of U.S. Non-Provisional application Ser. No. 13/661,618, filed Oct. 26, 2012, which claims the benefit of priority of U.S. Provisional Application Ser. No. 61/552,581, filed Oct. 28, 2011, the disclosure of which is hereby incorporated by reference in its entirety.

SEQUENCE LISTING

The instant application contains a Sequence Listing which has been submitted in ASCII format via EFS-Web and is hereby incorporated by reference in its entirety. Said ASCII copy, created on Dec. 13, 2012, is named 22441US2.txt and is 3,860 bytes in size.

FIELD OF THE INVENTION

The present invention relates to a construct comprising nucleotide sequences encoding enzyme activities involved in the dopamine synthesis pathway. At least two of the nucleotide sequences are operably linked such that they encode a fusion protein. The invention also provides a viral vector genome, vector production system and viral vector particle comprising such a nucleotide sequence. Expression of the nucleotide sequence in vivo, for example by gene therapy using a viral vector particle, causes dopamine synthesis which is useful in the treatment and/or prevention of neurological disorders characterised by a reduction or loss of dopamine-producing neurons, such as Parkinson's disease.

BACKGROUND TO THE INVENTION

Parkinson's disease (PD) is a neurodegenerative disorder that is characterised by the loss of dopaminergic neurons in the substantia nigra. This ultimately leads to dopamine depletion in the striatum causing severe motor deficits. One treatment of Parkinson's disease is the oral administration of L-DOPA, the precursor to dopamine, which can restore a degree of the motor function. However, as the disease progresses, L-DOPA therapy becomes less effective in the treatment of the motor deficits, requiring higher doses to be used which have severe side effects.

Improved treatment of PD could be achieved by the release of dopamine directly to the striatum. This may be achieved by gene therapy. Gene therapy is attractive for the treatment of PD because specific protein production can be targeted to specific areas of the CNS such as the striatum. Synthesis of dopamine from the amino acid tyrosine involves the enzymes tyrosine hydroxylase (TH), which catalyses the synthesis of L-DOPA from tyrosine and aromatic amino acid decarboxylase (AADC), which converts L-DOPA to dopamine. The TH step is thought to be rate limiting. TH requires a cofactor in order to function, tetrahydrobiopterin ($BH_4$), the synthesis of which is catalyzed by the enzyme GTP-cyclohydrolase 1 (CH-1).

Gene therapy approaches using Adeno-associated virus (AAV) vectors to deliver single genes from the dopamine biosynthetic pathway have been investigated with some behavioural benefit in PD animal models (Leff et al., 1999 Neuroscience 92, 185-196; Bankiewicz et al., 2006 Mol Ther 14, 564-570). Further approaches showed that simultaneous delivery of two or more of the enzymes that mediate dopamine synthesis demonstrated greater efficacy in animal models of PD (Fan et al., 1998 Hum Gene Ther 9, 2527-2535.; Shen et al., 2000 Hum Gene Ther 11, 1509-1519.; Muramatsu et al., 2002 Hum Gene Ther 13, 345-354).

This led to the theory that if all three dopamine synthesizing enzymes could be expressed in conjunction and in the same cell then the dopamine synthesis would be greater and would lead to a greater efficacy in PD. However, due to the limited packaging capacity of AAV vectors the number of genes that can be delivered is limited. Thus, it was decided to use a lentiviral vector (LV) for this purpose as the packaging capacity of these vectors is much greater. Lentiviral vectors (LV) are particularly advantageous for gene therapy approaches to the central nervous system (CNS) because of their ability to stably transduce non-dividing cell types such as neurons. LVs derived from non-primate lentiviruses, not known to be infectious or pathogenic for humans, such as equine infectious anaemia virus (EIAV), have been developed and their ability to transduce non-dividing cells established. ProSavin® is an Equine Infectious Anaemia Virus (EIAV) based LV for the treatment of PD. The genome of ProSavin® is a tricistronic construct comprising the coding sequences for the three key dopamine biosynthetic enzymes, TH, AADC and CH1 operably linked by two internal ribosome entry sites (IRES). ProSavin® is currently under evaluation in a phase I/II clinical trial with vector material that was generated in a process comprising three plasmid transient co-transfections of HEK293T cells (Mitrophanous et al., 1999 Gene Ther 6, 1808-1818).

A goal of any gene therapy approach is to increase the titre of the vector, so that lower volumes of vector preparation may be used. This is a particularly desirable outcome in a ProSavin®-type treatment, where the vector is injected directly into the brain, necessitating the use of small volumes.

The complex secondary structures of IRES elements may act as an impediment to efficient reverse transcription. The present inventors therefore hypothesised that removal of the IRES elements should increase the titre of the vectors. One option would be to replace the IRES elements with sequences encoding short peptide sequences (linkers) to generate fusion proteins comprising two or more of the three enzyme activities required for dopamine synthesis. However, as the native form of TH exists as a homotetramer (Goodwill et al., 1997 Nat Struct Biol 4, 578-585) and that of CH1 as a homodecamer (Nar et al., 1995 Structure 3, 459-466; Steinmetz et al., 1998 J Mol Biol 279, 189-199), fusion of these enzymes with each other or with other enzymes such as AADC might prevent the correct tertiary structure formation of the enzymes which may then inhibit enzyme function or prevent them from functioning at maximal capacity. In support of this, it has been previously reported that a fusion between TH and (3-galactosidase is enzymatically inactive (Wu and Cepko (1994) J Neurochem 62:863-72).

Surprisingly, the present inventors found that fusion of two or all three of the dopamine synthesising enzymes lead to i) functional enzymes; and ii) an enhanced dopamine biosynthetic pathway for some constructs resulting in elevated levels of L-DOPA and/or dopamine production. In particular, enhanced dopamine production was observed for some constructs when compared to the levels obtained using the construct with all three genes encoding the dopamine synthesising enzymes separated by IRES sequences. Contrary to expectations, for many constructs, the improvement resulting from these fusion designs was not associated with an increase in vector titre indicating that the IRES sequences were not having an inhibitory effect on titre. Furthermore, the increased levels of L-DOPA and dopamine were not due to increases in protein expression from the fusion design vectors suggesting that the fusion design had a higher specific activity.

DESCRIPTION OF THE FIGURES

FIG. 2*a* shows results from DNA integration assay to assess vector titre. FIG. 2*b* shows results from HPLC analysis to assess catecholamine production.

FIG. 3*a* shows results from DNA integration assay to assess vector titre. FIG. 3*b* shows results from HPLC analysis to assess production in HEK293T cells.

FIG. 5*a* shows results from DNA integration assay to assess vector titre. FIG. 5*b* shows results from HPLC analysis to assess catecholamine production in HEK293T cells.

FIG. 6*a* shows western blot analysis to examine expression of TH. FIG. 6*b* shows western blot analysis to examine expression of CH1. FIG. 6*c* shows western blot analysis to examine expression of AADC.

FIG. 7 discloses SEQ ID NOS 9-10, respectively, in order of appearance.

FIG. 8*a* shows western blot analysis to examine expression of TH. FIG. 8*b* shows western blot analysis to examine expression of CH1. FIG. 8*c* shows western blot analysis to examine expression of AADC. The correct band size for TH fused to CH1 is 68 kDa and although bands in these lanes can be seen there is a non-specific band in all the other lanes at this size. However, the bands are darker in intensity than the non-specific bands.

FIG. 10*a* shows EIAV-GFP transduced striatal neurons (MOI 1). FIG. 10*b* shows catecholamine production from striatal neurons transduced with vector.

FIG. 11*a* shows results from DNA integration assay to assess vector titre. FIG. 11*b* shows results from HPLC analysis to assess catecholamine production from HEK293T cells.

FIG. 12*a* shows images from human primary cortical neurons transduced with EIAV-GFP vector at MOIs 2 and 10. FIG. 12*b* shows catecholamine production from human primary cortical neurons transduced with EIAV vector at MOIs 0.4 (GFP background levels subtracted)–harvest 1 (5 days post transduction).

FIG. 13*a* shows western blot analysis to examine expression of TH. FIG. 13*b* shows western blot analysis to examine expression of AADC.

SUMMARY OF ASPECTS OF THE INVENTION

Figure 1:
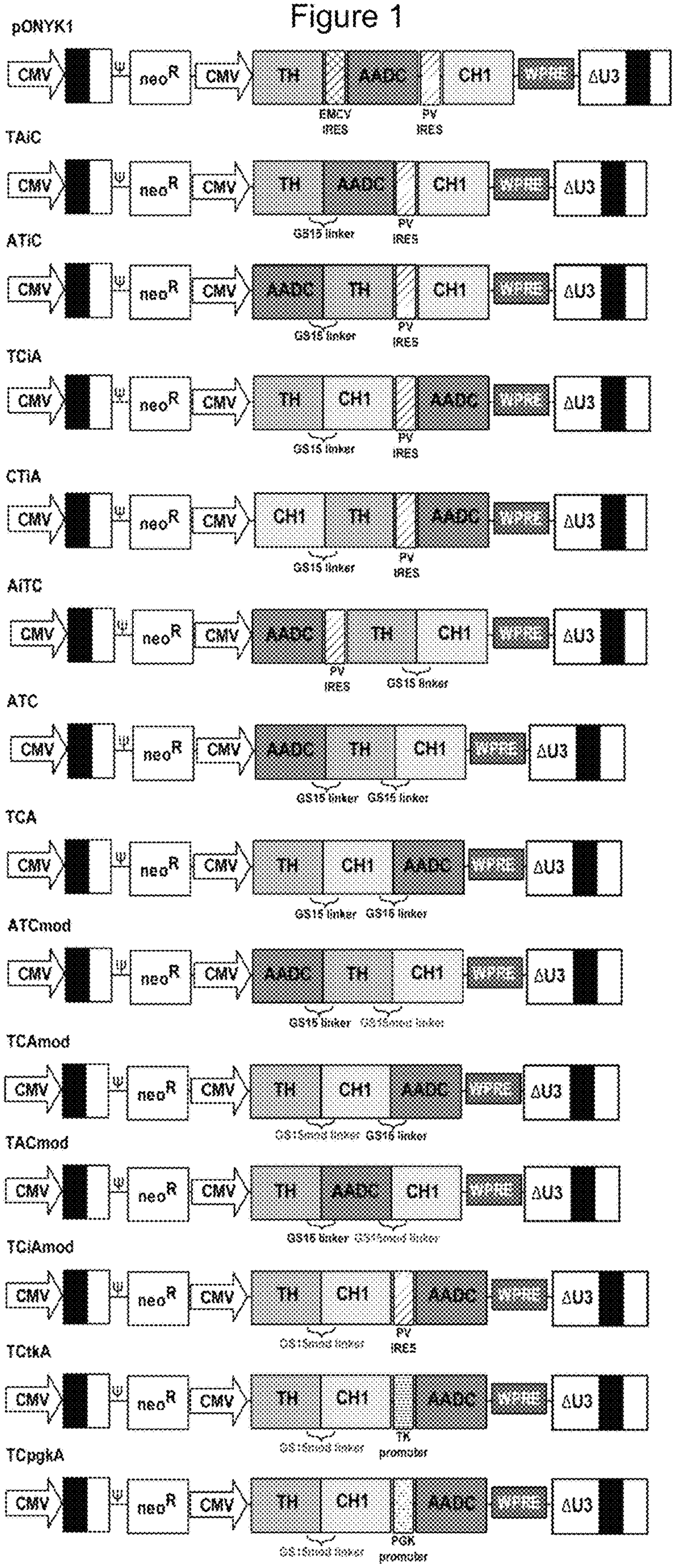
FIG. 1 shows a schematic representation of genomes encoding dopamine enzyme fusions.

The present inventors have tested a number of constructs comprising the dopamine synthesising enzymes tyrosine hydroxylase (TH), GTP-cyclohydrolase I (CH1) Aromatic Amino Acid Dopa Decarboxylase (AADC), which comprise a fusion of at least two out of the three genes.

As a result of this study, two clear themes have emerged:

i) constructs having TH linked to CH1 in that order (i.e. to form a TH-CH1 fusion protein) give high absolute levels of catecholamine production; and ii) constructs having AADC and TH linked in either order (i.e. to form an AADC-TH or TH-AADC fusion protein) give highly efficient conversion of L-DOPA to dopamine. The ratios of dopamine:L-DOPA associated with such constructs are high.

In a first embodiment of the first aspect of the invention, the present invention provides a construct comprising (i) a nucleotide sequence which encodes tyrosine hydroxylase (TH), (ii) a nucleotide sequence which encodes GTP-cyclohydrolase I (CH1) and (iii) a nucleotide sequence which encodes Aromatic Amino Acid Dopa Decarboxylase (AADC) wherein the nucleotide sequence encoding TH is linked to the nucleotide sequence encoding CH1 such that they encode a fusion protein TH-CH1.

The construct may be selected from the following:

TH-$_L$-CH1-$_{IRES}$-AADC;
AADC-$_L$-TH-$_L$-CH1;
TH-$_L$-CH1-$_p$-AADC; and
TH-L-CH1-p-AADC
L=linker-encoding sequence
IRES=Internal Ribosome Entry Site
P=promoter.

The construct preferably does not comprise an IRES upstream of the TH-CH1 encoding sequence to initiate translation of the TH-CH1 fusion protein.

In a second embodiment of the first aspect of the invention, the present invention provides a construct comprising (i) a nucleotide sequence which encodes tyrosine hydroxylase (TH), (ii) a nucleotide sequence which encodes GTP-cyclohydrolase I (CH1) and (iii) a nucleotide sequence which encodes Aromatic Amino Acid Dopa Decarboxylase (AADC) wherein the nucleotide sequence encoding AADC is operably linked to the nucleotide sequence encoding TH such that they encode a AADC-TH or TH-AADC fusion protein.

The construct may be selected from the following:

TH$_{-L-}$AADC$_{-IRES-}$CH1
AADC$_{-L-}$TH$_{-IRES-}$CH1
AADC$_{-L-}$TH1$_{-L-}$CH1
TH1$_{-L-}$AADC$_{-L-}$CH1
L=linker-encoding sequence
IRES=Internal Ribosome Entry Site.

The construct may comprise a linker which is not codon optimised for human usage.

The construct may comprise a linker which comprises the sequence shown as SEQ ID No. 1 or the sequence shown as SEQ ID No. 3.

The construct may have the sequence AADC-L1-TH-L2-CH1 or TH-L1-AADC-L2-CH1 wherein L1 and L2 are two different linker sequences. The nucleic acid sequence of L1 and L2 may be different, but the amino acid sequence of L1 and L2 may be the same. In the alternative, L1 and L2 may have the same nucleotide sequence. L1 and L2 may be selected from SEQ ID No. 1 or SEQ ID No. 3

Where the construct comprises a promoter, the promoter may, for example, be a constitutive promoter or a tissue-specific promoter. Examples of constitutive promoters include CMV promoter, phosphoglycerate kinase promoter and thymidine kinase promoter.

In a second aspect, the present invention provides a viral vector genome comprising a construct according to the first aspect of the invention.

The viral vector genome may, for example, be a lentiviral vector genome or an adeno associated viral vector genome.

In a third aspect the present invention provides a viral vector system comprising a genome according to the second aspect of the invention.

The viral vector system may, for example, be a lentiviral vector system or an adeno associated viral vector system.

The lentiviral vector system may comprise:

i) a genome according to the second aspect of the invention;

ii) a nucleotide sequence or sequences coding for gag and pol proteins;

iii) nucleotide sequences encoding other essential viral packaging components not encoded by the nucleotide sequence of ii).

In a fourth aspect, the present invention provides a method for producing a lentiviral particle which method comprises introducing into a producer cell:

iv) a genome according to the second aspect of the invention, v) a nucleotide sequence or sequences coding for gag and pol proteins; and vi) nucleotide sequences encoding other essential viral packaging components not encoded by one or more of the nucleotide sequences of ii).

In a fifth aspect, the present invention provides a viral particle produced by the system of the third aspect of the invention or by the method of the fourth aspect of the invention, which comprises NOIs encoding the dopamine synthesis enzymes GTP-cyclohydrolase I (CH1), Tyrosine Hydroxylase (TH), and Aromatic Amino Acid Dopa Decarboxylase (AADC), at least two of which are present as a fusion protein.

There is also provided a viral vector particle according to the fifth aspect of the invention which is an EIAV vector particle and which is pseudotyped with VSV-G.

In a sixth aspect, the present invention provides a pharmaceutical composition comprising a viral particle according to the fifth aspect of the invention, together with a pharmaceutically acceptable carrier or diluent.

In a seventh aspect, the present invention provides a method for producing dopamine in vivo, which comprises the step of expressing the dopamine synthesis enzymes GTP-cyclohydrolase I (CH1), Tyrosine Hydroxylase (TH), and Aromatic Amino Acid Dopa Decarboxylase (AADC) in the subject from a construct according to the first aspect of the invention.

In an eighth aspect, the present invention provides a method for treating and/or preventing a neurodegenerative disease or a disease where dopamine levels are reduced in a subject which comprises the step of administering a viral particle according to the fifth aspect of the invention or a pharmaceutical composition according to the sixth aspect of the invention to the subject.

In a ninth aspect, the present invention provides a viral particle according to the fifth aspect of the invention or a pharmaceutical composition according to the sixth aspect of the invention for use in treating and/or preventing a neurodegenerative disease in a subject by inducing in vivo dopamine synthesis.

The neurodegenerative disease may be Parkinson's disease. The disease where dopamine levels are reduced may by Lesch-Nyhan syndrome.

In a tenth aspect, the present invention provides a nucleotide sequence encoding a linker having the amino acid sequence shown as SEQ ID No. 2, but which nucleotide sequence has a different sequence to that shown in SEQ ID No. 3.

The nucleotide sequence may lack the codon pair GGA GGC.

The nucleotide sequence may comprise the sequence shown as SEQ ID No. 1.

DETAILED DESCRIPTION

Construct

The first aspect of the present invention relates to a construct.

The nucleotide sequence comprises three nucleotide sequences of interest (NOIs), each of which encodes an enzyme activity.

The construct may be a DNA or RNA sequence, such as for example a synthetic RNA/DNA sequence, a recombinant RNA/DNA sequence (i.e. prepared by use of recombinant DNA techniques), a cDNA sequence or a partial genomic DNA sequence, including combinations thereof.

The present invention also encompasses vectors, such as plasmids, comprising the construct of the present invention.

NOI

Each NOI in the construct encodes an enzyme involved in dopamine synthesis. The NOIs encode tyrosine hydroxylase (TH), GTP-cyclohydrolase I (CH1) and Aromatic Amino Acid Dopa Decarboxylase (AADC).

The sequences of all three enzymes are available: Accession Nos. X05290, U19523 and M76180 respectively.

The NOI may encode all or part of the dopamine synthesis enzyme. For example, the NOI may encode a truncated version of the protein which retains enzymatic activity.

Full length TH comprises a catalytic domain, a tetramerization domain and a N-terminal regulatory domain. The TH-encoding NOI of the vector of the present invention may encode a truncated TH that contains the catalytic and tetramerization domain, but lacks a functional N-terminal regulatory domain.

This form of TH avoids feed-back inhibition by dopamine which may limit activity of the full-length enzyme.

The NOI may encode a mutant, homologue or variant of the dopamine synthesis enzyme.

The term "mutant" includes enzymes which include one or more amino acid variations from the wild-type sequence. For example, a mutant may comprise one or more amino acid additions, deletions or substitutions. A mutant may arise naturally, or may be created artificially (for example by site-directed mutagenesis).

Here, the term "homologue" means a protein having a certain homology with the dopamine synthesis enzyme. Here, the term "homology" can be equated with "identity".

In the present context, a homologous sequence may be at least 75, 85 or 90% identical or at least 95 or 98% identical to the subject sequence at the amino acid or nucleotide level. Typically, the homologues will comprise or encode the same active sites etc. as the subject sequence. Identity comparisons may be conducted, for example, using the BLAST software.

The NOI may be codon optimised.

Linkers

The lentiviral vector genome of the present invention comprises three NOIs encoding dopamine synthesis enzymes. At least two of the NOIs are joined by a linker-encoding sequence (L), such that the genome encodes a fusion protein comprising the enzyme amino acid sequences.

A suitable linker may comprise amino acid repeats such as glycine-serine repeats. The purpose of the linker is to allow the correct formation and/or functioning of the enzymes. It should be sufficiently flexible and sufficiently long to achieve that purpose. Since the NOIs encode different enzymes, the linker needs to be chosen to allow the functioning of both of the enzymes. The coding sequence of the flexible linker may be chosen such that it encourages translational pausing and therefore independent folding of the protein products of the NOIs.

A person skilled in the art will be able to design linker-encoding sequences suitable for use in the nucleotide sequence of the invention. Some specific examples of suitable linkers are given below, but the invention is not limited to these particular linkers.

1.
(SEQ ID NO: 2)
(Gly-Gly-Gly-Gly-Ser)$_3$ as described in Somia et al., 1993 PNAS 90, 7889.

2.
(SEQ ID NO: 4)
(Gly-Gly-Gly-Gly-Ser)$_5$.

3.
(SEQ ID NO: 5)
(Asn-Phe-Ile-Arg-Gly-Arg-Glu-Asp-Leu-Leu-Glu-Lys-Ile-Ile-Arg-Gln-Lys-Gly-Ser-Ser-Asn) from HSF-1 of yeast, see Wiederrecht et al., 1988 Cell 54, 841.

4.
(SEQ ID NO: 6)
(Asn-Leu-Ser-Ser-Asp-Ser-Ser-Leu-Ser-Ser-Pro-Ser-Ala-Leu-Asn-Ser-Pro-Gly-Ile-Glu-Gly-Leu-Ser) from POU-specific OCT-1, see Dekker et al., 1993 Nature 362, 852 and Sturm et al., 1988 Genes and Dev. 2, 1582.

-continued 5.
(SEQ ID NO: 7)
(Gln-Gly-Ala-Thr-Phe-Ala-Leu-Arg-Gly-Asp-Asn-Pro-GlnGly) from RGD-containing Laminin peptide, see Aumailly et al., 1990 FEES Lett.262, 82.

6.
(SEQ ID NO: 8)
(Ser-Gly-Gly-Gly-Glu-Ile-Leu-Asp-Val-Pro-Ser-Thr-Gly-GlySer-Ser-Pro-Gly) from LDV-containing linker, see Wickham et al., Gene Therapy 1995 2, 750.

The following GS15 flexible linker may be used: (Gly-Gly-Gly-Gly-Ser)$_3$ (SEQ ID NO: 2). GS5, GS15, and GS30 linkers may also be suitable.

In constructs which comprise two linkers, i.e. all three enzymes are linked to be expressed as one fusion protein, two non-identical linker-encoding sequences may be chosen, alternatively the linker sequences may be identical. The linker sequences may be identical at the amino acid level, but their encoding nucleic acid sequences may be different due to degeneracy in the genetic code.

As shown in the Examples below, the use of a modified GS15 linker-encoding sequence (GS15mod) between the TH and CH1 genes resulted in an increase in catecholamine production with both constructs despite no evidence for an increase in protein expression.

The linker-encoding sequence used in the nucleotide sequence of the present invention may be a modified form of a linker-encoding sequence, such as one which encodes GS5, GS15, and GS30, which is not codon optimised for human usage.

The linker-encoding sequence may comprise the following sequence:

(SEQ ID No. 1)
GGAGGTGGCGGGTCCGGGGGCGGGGGTAGCGGTGGCGGGGGCTCC.

The tenth aspect of the invention relates to a nucleotide sequence encoding a linker having the amino acid sequence shown as SEQ ID No. 2, but which nucleotide sequence has a different sequence to that shown in SEQ ID No. 3.

(SEQ ID No. 2)
(Gly-Gly-Gly-Gly-Ser)$_3$.

(SEQ ID No. 3)
GGGGGAGGCGGTAGCGGCGGAGGGGGCTCCGGCGGAGGCGGGAGC.

The construct may comprise the sequence shown as SEQ ID No. 1 (above).

IRES

When located between open reading frames in an mRNA, an IRES allows translation of the downstream open reading frame by promoting entry of the ribosome at the IRES element followed by downstream initiation of translation. The use of IRES elements in retroviral vectors has been investigated (see, for example, WO 93/0314). Suitable IRES sequences for use in lentiviral vectors are described in WO 02/29065.

Promoter

An IRES may be replaced with a promoter, especially to control expression of the AADC gene. In configurations where AADC expression is under the control of an IRES, AADC levels may limit dopamine production.

Expression of a NOI may be controlled using control sequences, which include promoters/enhancers and other expression regulation signals. Prokaryotic promoters and promoters functional in eukaryotic cells may be used. Tissue specific or stimuli specific promoters may be used. Chimeric promoters may also be used comprising sequence elements from two or more different promoters.

Suitable promoting sequences are strong promoters including those derived from the genomes of viruses—such as polyoma virus, adenovirus, fowlpox virus, bovine papilloma virus, avian sarcoma virus, cytomegalovirus (CMV), retrovirus and Simian Virus 40 (SV40)—or from mammalian cellular promoters—such as the actin promoter or ribosomal protein promoter. Transcription of a gene may be increased further by inserting an enhancer sequence into the vector. Enhancers are relatively orientation and position independent; however, one may employ an enhancer from a eukaryotic cell virus—such as the SV40 enhancer on the late side of the replication origin (bp 100-270) and the CMV early promoter enhancer. The enhancer may be spliced into the vector at a position 5' or 3' to the promoter, but is preferably located at a site 5' from the promoter.

The promoter can additionally include features to ensure or to increase expression in a suitable host. For example, the features can be conserved regions e.g. a Pribnow Box or a TATA box. The promoter may even contain other sequences to affect (such as to maintain, enhance, decrease) the levels of expression of a nucleotide sequence. Suitable other sequences include the Sh1-intron or an ADH intron. Other sequences include inducible elements—such as temperature, chemical, light or stress inducible elements. Also, suitable elements to enhance transcription or translation may be present.

The promoter may, for example, be constitutive or tissue specific.

Constitutive Promoter

Examples of suitable constitutive promoters include CMV promoter, RSV promoter, phosphoglycerate kinase (PGK) and thymidine kinase (TK) promoters.

Tissue Specific Promoter

Examples of suitable tissue specific promoters include Synapsin 1, Enolase, α-calcium/calmodulin-dependent protein kinase II and GFAP Fusions The construct of the present invention comprises NOIs encoding TH, AADC and CH1. Two of the three, or all three, enzymes may be fused, for example, by using a flexible linker. Where two enzymes are fused the NOI encoding the third enzyme may be operably linked to the nucleotide sequence encoding the fusion protein by, for example, an IRES. The IRES may be positioned 5' or 3' to the nucleotide sequence encoding the fusion protein. Alternatively, the NOI encoding the third enzyme may be operatively linked to a promoter.

The present inventors have found that:

vii) constructs having TH linked to CH1 in that order (i.e. to form a TH-CH1 fusion protein) give high absolute levels of catecholamine production; and viii) constructs having AADC and TH linked in either order (i.e. to form a AADC-TH or TH-AADC fusion protein) give highly efficient conversion of L-DOPA to dopamine.

It is important to consider the amount of protein (i.e. enzymes) produced with each construct. For some constructs, the absolute levels of protein produced were low, but levels of L-DOPA and/or dopamine were relatively high. This indicates that the efficiency of the enzymes in that particular configuration is high, because a lower amount of enzymes is giving rise to comparable amounts of L-DOPA/dopamine.

Table 1 shows total catecholamine production for each construct following transduction of neuronal cells. The constructs are ranked according to total catecholamine production. The catecholamine production for pONYK1 in the same experiment is shown in brackets.

| Construct | Catecholoamine production (ng/ml) | Neuronal cell type | FIG. |
|---|---|---|---|
| TCiA | 80.1 (0.5) | Rat striatal neurons | 10b |
| ATCmod | 25.6 (0.5) | Rat striatal neurons | 10b |
| TCtkA | 25.5 (0.6) | Primary cortical neurons (human) | 12b |
| CTiA | 10.8 (0.5) | Rat striatal neurons | 10b |
| ATC | 8.6 (0.5) | Rat striatal neurons | 10b |
| TCiAmod | 5.6 (0.6) | Primary cortical neurons (human) | 12b |
| TAiC | 5.2 (0.5) | Rat striatal neurons | 10b |
| TACmod | 2.9 (0.6) | Primary cortical neurons (human) | 12b |
| TCAmod | 2 (0.5) | Rat striatal neurons | 10b |
| TCA | 1.6 (0.5) | Rat striatal neurons | 10b |
| ATiC | 0.7 (0.5) | Rat striatal neurons | 10b |

Table 2 shows the dopamine:L-DOPA ratio for each construct following transduction of neuronal cells. The constructs are ranked according to dopamine:L-DOPA ratio. The dopamine:L-DOPA ratio for pONYK1 in the same experiment is shown in brackets.

| Construct | Dopamine:L-DOPA ratio | Neuronal cells | FIG. |
|---|---|---|---|
| TACmod | 28 (—)* | Primary cortical neurons (human) | 12b |
| ATCmod | 5.2 (0.7) | Rat striatal neurons | 10b |
| ATC | 3.5 (0.7) | Rat striatal neurons | 10b |
| TCiAmod | 2.7 (—)* | Primary cortical neurons (human) | 12b |
| TAiC | 1.7 (0.7) | Rat striatal neurons | 10b |
| ATiC | 1.3 (0.7) | Rat striatal neurons | 10b |
| TCAmod | 1 (0.7) | Rat striatal neurons | 10b |
| TCA | 0.5 (0.7) | Rat striatal neurons | 10b |
| TCiA | 0.1 (0.7) | Rat striatal neurons | 10b |
| CTiA | 0.01 (0.7) | Rat striatal neurons | 10b |
| TCtkA | 0.01 (—)* | Primary cortical neurons (human) | 12b |

No L-DOPA detectable for pONYK1 after correction for background levels

The construct CTiA does not show improved performance.

Without wishing to be bound by theory, the inventors consider the reason that TCiA showed improved performance but CTiA did not is because the order of the enzymes in the TC fusion is important. The construct of the present invention may therefore encode a fusion of TH and CH1 in the order TC, rather than CT.

The construct may be selected from the following:

TH-$_{L}$-CH1-$_{IRES}$-AADC;
AADC-$_{L}$-TH-$_{L}$-CH1;
TH$_{-L-}$CH1$_{-L-}$AADC; and
TH$_{-L-}$CH1$_{-P-}$AADC
TH$_{-L-}$AADC$_{-IRES-}$CH1
AADC$_{-L-}$TH$_{-IRES-}$CH1
TH1$_{-L-}$AADC$_{-L-}$CH1
L=linker-encoding sequence IRES=Internal Ribosome Entry Site P=promoter As mentioned above, TH comprises a catalytic domain, a tetramerization domain and an N-terminal regulatory domain.

The TH-encoding NOI may encode a truncated TH that contains the catalytic and tetramerization domain, but which lacks a functional N-terminal regulatory domain.

Figure 7:
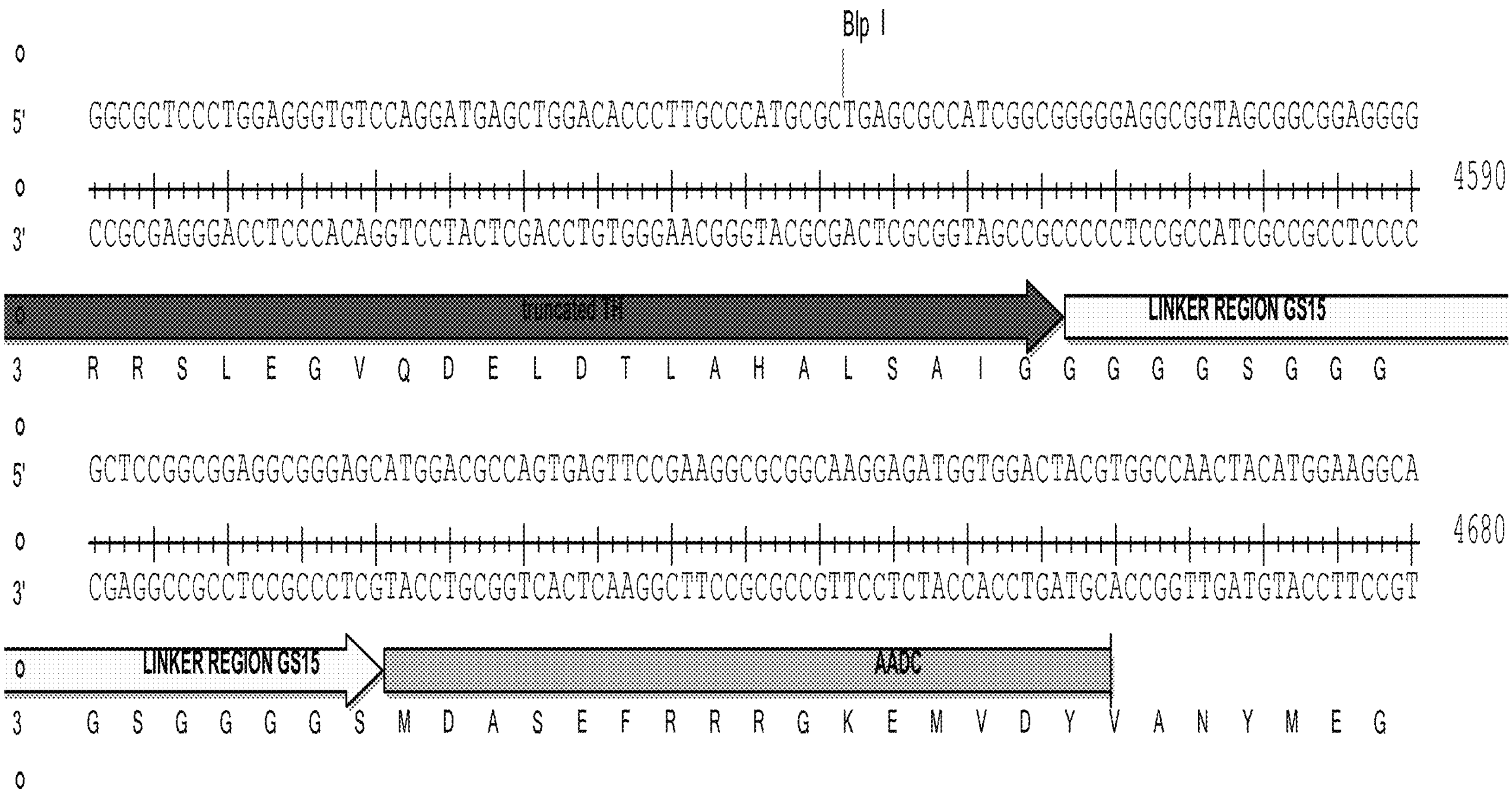
FIG. 7 is a diagram showing the linkage of a truncated version of TH to AADC via a GS15 linker.

FIG. 7 shows the sequence of a construct in which the C-Terminus of a truncated version of TH is fused via a GS15 linker to the N-terminus of AADC.

Alternatively the CH1 may be fused via its N terminus leaving its C-terminus free.

Viral Vectors

The present invention also provides a viral vector genome, such as a lentiviral vector genome or adeno-associated viral vector genome comprising a nucleotide sequence according to the first aspect of the invention. The present invention also provides a viral vector production system and vector particle comprising such a genome.

The viral vector of the present invention may be derived or derivable from any suitable virus. A recombinant viral particle is capable of transducing a target cell with a nucleotide sequence of interest (NOI).

For a retroviral particle, once within the cell the RNA genome from the vector particle is reverse transcribed into DNA and integrated into the genome of the target cell.

Lentiviral Vectors

Lentiviruses are part of a larger group of retroviruses. A detailed list of lentiviruses may be found in Coffin et al. (1997) "Retroviruses" Cold Spring Harbor Laboratory Press Eds: J M Coffin, SM Hughes, HE Varmus pp 758-763). In brief, lentiviruses can be divided into primate and non-primate groups. Examples of primate lentiviruses include but are not limited to: the human immunodeficiency virus (HIV), the causative agent of acquired immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV), feline immunodeficiency virus (FIV) and bovine immunodeficiency virus (BIV).

Lentiviruses differ from other members of the retrovirus family in that lentiviruses have the capability to infect both dividing and non-dividing cells (Lewis et al (1992) EMBO J 11(8):3053-3058) and Lewis and Emerman (1994) J Virol 68 (1):510-516). In contrast, other retroviruses—such as MLV—are unable to infect non-dividing or slowly dividing cells such as those that make up, for example, muscle, eye, brain, lung and liver tissue.

A lentiviral vector, as used herein, is a vector which comprises at least one component part derivable from a lentivirus. Preferably, that component part is involved in the biological mechanisms by which the vector infects cells, expresses genes or is replicated.

The basic structure of retrovirus and lentivirus genomes share many common features such as a 5' LTR and a 3' LTR, between or within which are located a packaging signal to enable the genome to be packaged, a primer binding site, attachment sites to enable integration into a host cell genome and gag, pol and env genes encoding the packaging components—these are polypeptides required for the assembly of viral particles. Lentiviruses have additional features, such as rev and RRE sequences in HIV, which enable the efficient export of RNA transcripts of the integrated provirus from the nucleus to the cytoplasm of an infected target cell.

In the provirus, the viral genes are flanked at both ends by regions called long terminal repeats (LTRs). The LTRs are responsible for transcription by serving as enhancer-promoter sequences and polyadenylation signals thereby controlling the expression of the viral genes.

The LTRs themselves are identical sequences that can be divided into three elements, which are called U3, R and U5. U3 is derived from the sequence unique to the 3' end of the RNA. R is derived from a sequence repeated at both ends of the RNA and U5 is derived from the sequence unique to the 5' end of the RNA. The sizes of the three elements can vary considerably among different viruses.

In a replication-defective lentiviral vector genome gag, pol and env may be absent or not functional.

In a typical lentiviral vector of the present invention, at least part of one or more protein coding regions essential for replication may be removed from the virus. This makes the viral vector replication-defective. Portions of the viral genome may also be replaced by an NOI in order to generate a vector comprising an NOI which is capable of transducing a target non-dividing host cell and/or integrating its genome into a host genome.

In one embodiment the lentiviral vectors are non-integrating vectors as described in WO 2007/071994.

In a further embodiment the vectors have the ability to deliver a sequence which is devoid of or lacking viral RNA. In a further embodiment a heterologous binding domain (heterologous to gag) located on the RNA to be delivered and a cognate binding domain on gag or pol can be used to ensure packaging of the RNA to be delivered. Both of these vectors are described in WO 2007/072056.

The lentiviral vector may be a "non-primate" vector, i.e., derived from a virus which does not primarily infect primates, especially humans.

The viral vector may be derived from EIAV. In addition to the gag, pol and env genes EIAV encodes three other genes: tat, rev, and S2. Tat acts as a transcriptional activator of the viral LTR (Derse and Newbold (1993) Virology 194(2):530-536 and Maury et al (1994) Virology 200(2):632-642) and Rev regulates and coordinates the expression of viral genes through rev-response elements (RRE) (Martarano et al. (1994) J Virol 68(5):3102-3111). The mechanisms of action of these two proteins are thought to be broadly similar to the analogous mechanisms in the primate viruses (Martarano et al. (1994) J Virol 68(5):3102-3111). The function of S2 is unknown. In addition, an EIAV protein, Ttm, has been identified that is encoded by the first exon of tat spliced to the env coding sequence at the start of the transmembrane protein (Beisel et al. (1993) J Virol 67(2):832-842).

The term "recombinant lentiviral vector" refers to a vector with sufficient lentiviral genetic information to allow packaging of an RNA genome, in the presence of packaging components, into a viral particle capable of infecting a target cell. Infection of the target cell may include reverse transcription and integration into the target cell genome. The recombinant lentiviral vector carries non-viral coding sequences which are to be delivered by the vector to the target cell. A recombinant lentiviral vector is incapable of independent replication to produce infectious lentiviral particles within the final target cell. Usually the recombinant lentiviral vector lacks a functional gag-pol and/or env gene and/or other genes essential for replication. The vector of the present invention may be configured as a split-intron vector. A split intron vector is described in PCT patent application WO 99/15683.

The recombinant lentiviral vector of the present invention may have a minimal viral genome.

As used herein, the term "minimal viral genome" means that the viral vector has been manipulated so as to remove the non-essential elements and to retain the essential elements in order to provide the required functionality to infect, transduce and deliver a nucleotide sequence of interest to a target host cell. Further details of this strategy can be found in our WO 98/17815.

In one embodiment of the present invention, the vector is a self-inactivating vector.

By way of example, self-inactivating retroviral vectors have been constructed by deleting the transcriptional enhancers or the enhancers and promoter in the U3 region of the 3' LTR. After a round of vector reverse transcription and integration, these changes are copied into both the 5' and the 3' LTRs producing a transcriptionally inactive provirus (Yu et al (1986) Proc. Natl. Acad. Sci. 83:3194-3198; Dougherty and Temin et al (1987) Proc. Natl. Acad. Sci. 84:1197-1201; Hawley (1987) Proc. Natl. Acad. Sci. 84:2406-2410 and Yee et al (1987) Proc. Natl. Acad. Sci. 91:9564-9568). However, any promoter(s) internal to the LTRs in such vectors will still be transcriptionally active. This strategy has been employed to eliminate effects of the enhancers and promoters in the viral LTRs on transcription from internally placed genes. Such effects include increased transcription (Jolly et al (1983) Nucleic Acids Res. 11:1855-1872) or suppression of transcription (Emerman and Temin (1984) Cell 39:449-467). This strategy can also be used to eliminate downstream transcription from the 3' LTR into genomic DNA (Herman and Coffin (1987) Science 236:845-848). This is of particular concern in human gene therapy where it is of critical importance to prevent the adventitious activation of an endogenous oncogene.

However, the plasmid vector used to produce the viral genome within a host cell/packaging cell will also include transcriptional regulatory control sequences operably linked to the lentiviral genome to direct transcription of the genome in a host cell/packaging cell. These regulatory sequences may be the natural sequences associated with the transcribed lentiviral sequence, i.e. the 5' U3 region, or they may be a heterologous promoter such as another viral promoter, for example the CMV promoter. Some lentiviral genomes require additional sequences for efficient virus production. For example, in the case of HIV, rev and RRE sequence are preferably included. However the requirement for rev and RRE may be reduced or eliminated by codon optimisation of gag-pol (as described in WO 01/79518) and/or the inclusion of an Open Reading Frame downstream of the LTR and upstream of the internal promoter (as described in WO 03/064665), for example neo has been used in the constructs shown in FIG. 1, however, the skilled person could use any suitable Open Reading Frame. Alternative sequences which perform the same function as the rev/RRE system are also known. For example, a functional analogue of the rev/RRE system is found in the Mason Pfizer monkey virus. This is known as the constitutive transport element (CTE) and comprises an RRE-type sequence in the genome which is believed to interact with a factor in the infected cell. The cellular factor can be thought of as a rev analogue. Thus, CTE may be used as an alternative to the rev/RRE system. Any other functional equivalents which are known or become available may be relevant to the invention. For example, it is also known that the Rex protein of HTLV-I can functionally replace the Rev protein of HIV-1. It is also known that Rev and Rex have similar effects to IRE-BP.

The lentiviral vector according to the present invention may consist of a self-inactivating minimal lentiviral vector, derived from Equine Infectious Anaemia Virus (EIAV), preferably encoding three enzymes that are involved in the dopamine synthetic pathway. The proteins encoded by such a vector may comprise a truncated form of the human tyrosine hydroxylase gene (which lacks the N-terminal 160 amino acids involved in feedback regulation of TH), the human aromatic L-amino-acid decarboxylase (AADC), and the human GTP-cyclohydrolase 1 (GTP-CH1) gene. The vector may be produced by the transient transfection of cells (e.g.HEK293T cells) with three plasmids, encoding for: (1) the vector genomes as described herein (2) the synthetic EIAV gag/pol expression vector (pESGPK, WO 01/79518 and WO 05/29065) and (3) the VSV-G envelope expression vector (pHGK)

Packaging Sequence

The term "packaging signal" which is referred to interchangeably as "packaging sequence" or "psi" is used in reference to the non-coding, cis-acting sequence required for encapsidation of lentiviral RNA strands during viral particle formation. In HIV-1, this sequence has been mapped to loci extending from upstream of the major splice donor site (SD) to at least the gag start codon.

As used herein, the term "extended packaging signal" or "extended packaging sequence" refers to the use of sequences around the psi sequence with further extension into the gag gene. The inclusion of these additional packaging sequences may increase the efficiency of insertion of vector RNA into viral particles.

Pseudotyping

The lentiviral vector of the present invention may be pseudotyped. In this regard, pseudotyping can confer one or more advantages. For example, with the lentiviral vectors, the env gene product of the HIV based vectors would restrict these vectors to infecting only cells that express a protein called CD4. But if the env gene in these vectors has been substituted with env sequences from other viruses, then they may have a broader infectious spectrum (Verma and Somia (1997) Nature 389(6648):239-242). By way of examples, Miller et al. pseudotyped a MoMLV vector with the envelope from the amphotropic retrovirus 4070A (Mol. Cell. Biol. 5:431-437) other workers have pseudotyped an HIV based lentiviral vector with the glycoprotein from VSV (Verma and Somia (1997) Nature 389(6648):239-242).

In another alternative, the Env protein may be a modified Env protein such as a mutant or engineered Env protein. Modifications may be made or selected to introduce targeting ability or to reduce toxicity or for another purpose (Marin et al (1996) J Virol 70(5):2957-2962; Nilson et al (1996) Gene Ther 3(4):280-286; and Fielding et al (1998) Blood 91(5):1802-1809 and references cited therein).

The vector may be pseudotyped, for example with a gene encoding at least part of the rabies G protein or the VSV-G protein.

VSV-G

The envelope glycoprotein (G) of Vesicular stomatitis virus (VSV), a rhabdovirus, is an envelope protein that has been shown to be capable of pseudotyping certain retroviruses including lentiviruses.

Its ability to pseudotype MoMLV-based retroviral vectors in the absence of any retroviral envelope proteins was first shown by Emi et al. (1991) J. Virol. 65:1202-1207). WO 94/294440 teaches that retroviral vectors may be successfully pseudotyped with VSV-G. These pseudotyped VSV-G vectors may be used to transduce a wide range of mammalian cells. More recently, Abe et al. (1998) J. Virol 72(8): 6356-6361 teach that non-infectious retroviral particles can be made infectious by the addition of VSV-G.

Burns et al (1993) Proc. Natl. Acad. Sci. USA 90:8033-8037) successfully pseudotyped the retrovirus MLV with VSV-G and this resulted in a vector having an altered host range compared to MLV in its native form. VSV-G pseudotyped vectors have been shown to infect not only mammalian cells, but also cell lines derived from fish, reptiles and insects (Burns et al (1993) Proc. Natl. Acad. Sci. USA 90:8033-8037). They have also been shown to be more efficient than traditional amphotropic envelopes for a variety of cell lines (Yee et al. (1994) Proc. Natl. Acad. Sci. USA 91:9564-9568 and Emi et al. (1991) J. Virol. 65:1202-1207). VSV-G protein can also be used to pseudotype certain lentiviruses and retroviruses because its cytoplasmic tail is capable of interacting with the retroviral cores.

The provision of a non-lentiviral pseudotyping envelope such as VSV-G protein gives the advantage that vector particles can be concentrated to a high titre without loss of infectivity (Akkina et al (1996) J. Virol. 70:2581-2585). Lentivirus and retrovirus envelope proteins are apparently unable to withstand the shearing forces during ultracentrifugation, probably because they consist of two non-covalently linked subunits. The interaction between the subunits may be disrupted by the centrifugation. In comparison the VSV glycoprotein is composed of a single unit. VSV-G protein pseudotyping can therefore offer potential advantages.

WO 00/52188 describes the generation of pseudotyped retroviral and lentiviral vectors, from stable producer cell lines, having vesicular stomatitis virus-G protein (VSV-G) as the membrane-associated viral envelope protein, and provides a gene sequence for the VSV-G protein.

Ross River Virus

The Ross River viral envelope has been used to pseudotype a non-primate lentiviral vector (FIV) and following systemic administration predominantly transduced the liver (Kang et al (2002) J Virol 76(18):9378-9388.). Efficiency was reported to be 20-fold greater than obtained with VSV-G pseudotyped vector, and caused less cytotoxicity as measured by serum levels of liver enzymes suggestive of hepatotoxicity.

Ross River Virus (RRV) is an alphavirus spread by mosquitoes which is endemic and epidemic in tropical and temperate regions of Australia. Antibody rates in normal populations in the temperate coastal zone tend to be low (6% to 15%) although sero-prevalence reaches 27 to 37% in the plains of the Murray Valley River system. In 1979 to 1980 Ross River Virus became epidemic in the Pacific Islands. The disease is not contagious between humans and is never fatal, the first symptom being joint pain with fatigue and lethargy in about half of patients (Fields Virology Fifth Edition (2007) Eds. Knipe and Howley. Lippincott Williams and Wilkins).

Baculovirus GP64

The baculovirus GP64 protein has been shown to be an attractive alternative to VSV-G for viral vectors used in the large-scale production of high-titre virus required for clinical and commercial applications (Kumar M, Bradow B P, Zimmerberg J (2003) Hum. Gene Ther. 14(1):67-77). Compared with VSV-G-pseudotyped vectors, GP64-pseudotyped vectors have a similar broad tropism and similar native titres. Because, GP64 expression does not kill cells, 293T-based cell lines constitutively expressing GP64 can be generated.

Rabies G

In the present invention the vector may be pseudotyped with at least a part of a rabies G protein or a mutant, variant, homologue or fragment thereof.

Teachings on the rabies G protein, as well as mutants thereof, may be found in WO 99/61639 and well as Rose et al (1982) J. Virol. 43:361-364, Hanham et al (1993) J. Virol. 67:530-542; Tuffereau et al (1998) J. Virol. 72:1085-1091, Kucera et al (1985) J. Virol. 55:158-162; Dietzschold et al (1983) PNAS 80:70-74; Seif et al (1985) J. Virol. 53:926-934; Coulon et al (1998) J. Virol. 72:273-278; Tuffereau et al (1998) J. Virol. 72:1085-10910; Burger et al (1991) J. Gen. Virol. 72:359-367; Gaudin et al (1995) J. Virol. 69:5528-5534; Benmansour et al (1991) J. Virol. 65:4198-4203; Luo et al (1998) Microbiol. Immunol. 42:187-193, Coll (1997) Arch. Virol. 142:2089-2097; Luo et al (1997) Virus Res. 51:35-41; Luo et al (1998) Microbiol. Immunol. 42:187-193; Coll (1995) Arch. Virol. 140:827-851; Tuchiya et al (1992) Virus Res. 25:1-13; Morimoto et al (1992) Virology 189:203-216; Gaudin et al (1992) Virology 187: 627-632; Whitt et al (1991) Virology 185:681-688; Dietzschold et al (1978) J. Gen. Virol. 40:131-139; Dietzschold et al (1978) Dev. Biol. Stand. 40:45-55; Dietzschold et al (1977) J. Virol. 23:286-293 and Otvos et al (1994) Biochim. Biophys. Acta 1224:68-76. A rabies G protein is also described in EP 0445625.

Alternative Envelopes

Other envelopes which can be used to pseudotype lentiviral vectors include Mokola, Ebola, 4070A and LCMV (lymphocytic choriomeningitis virus).

Adeno-Associated Viral Vectors

It had been known in the art that adeno-associated viral (AAV) vectors have limited packaging capacity therefore negatively impacting the number of genes that can be delivered efficiently. However, it is now known that this limitation is dependent on AAV serotype. For instance, capsids of AAV 5 and 7 serotypes can package genomes of up to 8 kb. This work has been described in U.S. Pat. No. 7,943,374. In addition, US 2009/0214478 describe AAV2/5 recombinant vectors with a packaging capacity up to 9 kb.

Features of AAV vectors are generally known to one of ordinary skill in the art. For example, AAV vectors have a broad host range and transduce both dividing and non-dividing cells with relatively low immunogenicity. It is also well known how to replace all AAV viral genes with a genetic cassette leaving in place only cis-acting AAV elements the Inverted Terminal Repeats (ITRs), the DNA packaging signal, and the replication origin. See e.g., Musatov et al., J. Virol., December 2002, 76(24). AAV can be packaged in producer cells when AAV gene products, Rep and Cap, and other accessory proteins are provided in trans. AAV packaging systems have been described. See, e.g., U.S. Pat. No. 5,139,941. Non-AAV accessory functions may be supplied by any of the known helper viruses such as Adenovirus, Herpes Simplex Virus, and vaccinia virus. Such AAV packaging systems have been described; e.g., in U.S. Pat. Nos. 4,797,368; 5,139,941; 5,866,552; 6,001,650; 6,723,551.

Codon Optimisation

The polynucleotides used in the present invention (including the NOI and/or vector components) may be codon optimised. Codon optimisation has previously been described in WO 99/41397 and WO 01/79518. Different cells differ in their usage of particular codons. This codon bias corresponds to a bias in the relative abundance of particular tRNAs in the cell type. By altering the codons in the sequence so that they are tailored to match with the relative abundance of corresponding tRNAs, it is possible to increase expression. By the same token, it is possible to decrease expression by deliberately choosing codons for which the corresponding tRNAs are known to be rare in the particular cell type. Thus, an additional degree of translational control is available.

Many viruses, including HIV and other lentiviruses, use a large number of rare codons and by changing these to correspond to commonly used mammalian codons, increased expression of a gene of interest, e.g. a NOI or packaging components in mammalian producer cells, can be achieved. Codon usage tables are known in the art for mammalian cells, as well as for a variety of other organisms.

Codon optimisation of viral vector components has a number of other advantages. By virtue of alterations in their sequences, the nucleotide sequences encoding the packaging components of the viral particles required for assembly of viral particles in the producer cells/packaging cells have RNA instability sequences (INS) eliminated from them. At the same time, the amino acid sequence coding sequence for the packaging components is retained so that the viral components encoded by the sequences remain the same, or at least sufficiently similar that the function of the packaging components is not compromised. In lentiviral vectors codon optimisation also overcomes the Rev/RRE requirement for export, rendering optimised sequences Rev independent. Codon optimisation also reduces homologous recombination between different constructs within the vector system (for example between the regions of overlap in the gag-pol and env open reading frames). The overall effect of codon optimisation is therefore a notable increase in viral titre and improved safety.

In one embodiment only codons relating to INS are codon optimised. However, in a much more preferred and practical embodiment, the sequences are codon optimised in their entirety, with some exceptions, for example the sequence encompassing the frameshift site of gag-pol (see below).

The gag-pol gene comprises two overlapping reading frames encoding the gag-pol proteins. The expression of both proteins depends on a frameshift during translation. This frameshift occurs as a result of ribosome "slippage" during translation. This slippage is thought to be caused at least in part by ribosome-stalling RNA secondary structures. Such secondary structures exist downstream of the frameshift site in the gag-pol gene. For HIV, the region of overlap extends from nucleotide 1222 downstream of the beginning of gag (wherein nucleotide 1 is the A of the gag ATG) to the end of gag (nt 1503). Consequently, a 281 bp fragment spanning the frameshift site and the overlapping region of the two reading frames is preferably not codon optimised. Retaining this fragment will enable more efficient expression of the gag-pol proteins.

For EIAV the beginning of the overlap has been taken to be nt 1262 (where nucleotide 1 is the A of the gag ATG). The end of the overlap is at 1461 bp. In order to ensure that the frameshift site and the gag-pol overlap are preserved, the wild type sequence has been retained from nt 1156 to 1465.

Derivations from optimal codon usage may be made, for example, in order to accommodate convenient restriction sites, and conservative amino acid changes may be introduced into the gag-pol proteins.

In one embodiment codon optimisation is based on lightly expressed mammalian genes. The third and sometimes the second and third base may be changed.

Due to the degenerate nature of the Genetic Code, it will be appreciated that numerous gag-pol sequences can be achieved by a skilled worker. Also there are many retroviral variants described which can be used as a starting point for generating a codon optimised gag-pol sequence. Lentiviral genomes can be quite variable. For example there are many quasi-species of HIV-1 which are still functional. This is also the case for EIAV. These variants may be used to enhance particular parts of the transduction process. Examples of HIV-1 variants may be found at the HIV Databases operated by Los Alamos National Security. Details of EIAV clones may be found at the National Center for Biotechnology Information (NCBI) database.

The strategy for codon optimised gag-pol sequences can be used in relation to any retrovirus. This would apply to all lentiviruses, including EIAV, FIV, BIV, CAEV, VMR, SIV, HIV-1 and HIV-2. In addition this method could be used to increase expression of genes from HTLV-1, HTLV-2, HFV, HSRV and human endogenous retroviruses (HERV), MLV and other retroviruses.

Codon optimisation can render gag-pol expression Rev independent. In order to enable the use of anti-rev or RRE factors in the lentiviral vector, however, it would be necessary to render the viral vector generation system totally Rev/RRE independent. Thus, the genome also needs to be modified. This is achieved by optimising vector genome components. Advantageously, these modifications also lead to the production of a safer system absent of all additional proteins both in the producer and in the transduced cell.

Activity

The fusion constructs of the invention produce functional dopaminergic synthesising enzymes and may cause an increase in dopamine production when compared to the levels obtained using a construct with all three genes encoding the dopamine synthesising enzymes separated by IRES sequences described in WO 02/29065.

The vector of the present invention may cause increased L-DOPA and/or dopamine production when expressed intracellularly than that of the vector described in WO 2001/04433, pONYK1.

The vector of the present invention may give at least 2, 3, 5, 10, 15, 20, 30, 40, 50, 60, 80, 80, 90, 100, 120, 130, 140, 150, 160, 200, 500, 1000-fold increase in dopamine and/or L-DOPA production.

The vector of the present invention may cause increased L-DOPA and/or dopamine production when compared to pONYK1 when expressed, for example, in HEK293T cells or PC-12 cells.

Dopamine or L-DOPA production may be measured by any of a number of methods known in the art, such as high performance liquid chromatography (HPLC).

Without wishing to be bound by theory, the present inventors suggest that L-DOPA and/or dopamine synthesis is increased by the fusion protein because the encoded proteins are physically close together, thereby facilitating their interactions with one another. This is particularly advantageous for enzymes of the dopamine biosynthetic pathway as physical proximity of each of the enzymes may facilitate efficient metabolite flow from one enzyme to the other enabling maximal L-DOPA or dopamine production.

As shown in the examples and summarised in Table 1 (above), some fusion constructs gave improved L-DOPA production and some gave improved dopamine production.

Pharmaceutical Composition

The lentiviral vector of the present invention may be provided in the form of a pharmaceutical composition. The pharmaceutical composition may be used for treating an individual by gene therapy, wherein the composition comprises a therapeutically effective amount of the lentiviral vector.

The viral preparation may be concentrated by ultracentrifugation. Alternatively, WO 2009/153563 describes methods for the downstream processing of lentiviral vectors. The resulting pharmaceutical composition may have at least $10^7$ TU./mL, for example from $10^7$ to $10^9$ TU./mL, or at least $10^9$ TU./mL. (The titer is expressed in transducing units per mL (TU./mL) as titred on standard D17 or HEK293T cell lines).

The pharmaceutical composition may be used to treat a human.

The composition may optionally comprise a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as (or in addition to) the carrier, excipient or diluent, any suitable binder(s), lubricant(s), suspending agent(s), coating agent(s), solubilising agent(s), and other carrier agents that may aid or increase the viral entry into the target site (such as for example a lipid delivery system).

Diseases

The viral vector may be used for treating a neurological condition. For example, the vector may be useful for the treatment and/or prevention of neurodegenerative diseases.

The disease may be treatable by the production of L-DOPA and/or dopamine in a subject.

The disease may be Parkinson's disease.

Treatment by gene therapy with vectors capable of delivering, for example, TH, GTP-CH1 and AADC, is likely to be particularly useful for the late stages of PD patients who have become refractory to oral L-DOPA treatment.

Certain constructs described herein increased the production of L-DOPA, and others increased the production of dopamine. Increased production of L-DOPA may be useful in patients who retain residual AADC enzymatic activity and are thus at least partly capable of converting L-DOPA to dopamine. These patients may be susceptible to conventional L-DOPA treatment. For example, $TH_{-L-}CH1_{-IRES-}AADC$ constructs produced high levels of both dopamine and L-DOPA, whereas $TH_{-L-}AADC_{-IRES-}CH1$, and $AADC_{-L-}TH_{-L-}CH1$ produced higher levels of dopamine relative to L-DOPA.

Increased production of dopamine may be useful in late-stage patients who lack sufficient endogenous AADC activity to process L-DOPA, and are thus less sensitive to conventional L-DOPA treatment.

The present invention also provides a method for selecting a therapy for a Parkinson's patient which comprises the step of selecting a vector according to the present invention based on its relative capacity to produce L-DOPA and dopamine.

Administration

The viral vector used in the present invention is administered to the brain, for example by injection into the caudate putamen.

The vector may be administered via one, two, three, four, five, six or more tracts per hemisphere.

In a previously described administration system for a lentiviral vector (Jarraya et al (2009) Sci Transl Med 14: 1(2) 2-4), the vector composition was administered in a discontinuous or "punctate" fashion, by administering an aliquot (4 μL) at the bottom of the tract, withdrawing the needle a little way, then administering a second aliquot (3 μL) and withdrawing the needle a little further, (second time); then administering a third aliquot (3 μL); thus aliquots had been deposited at 3 points along each needle tract delivering a total of 10 μL.

Alternatively the vector may be continuously infused as described in co-pending UK patent application No. 1009052.0.

The invention will now be further described by way of Examples, which are meant to serve to assist one of ordinary skill in the art in carrying out the invention and are not intended in any way to limit the scope of the invention.

EXAMPLES

Figure 2:
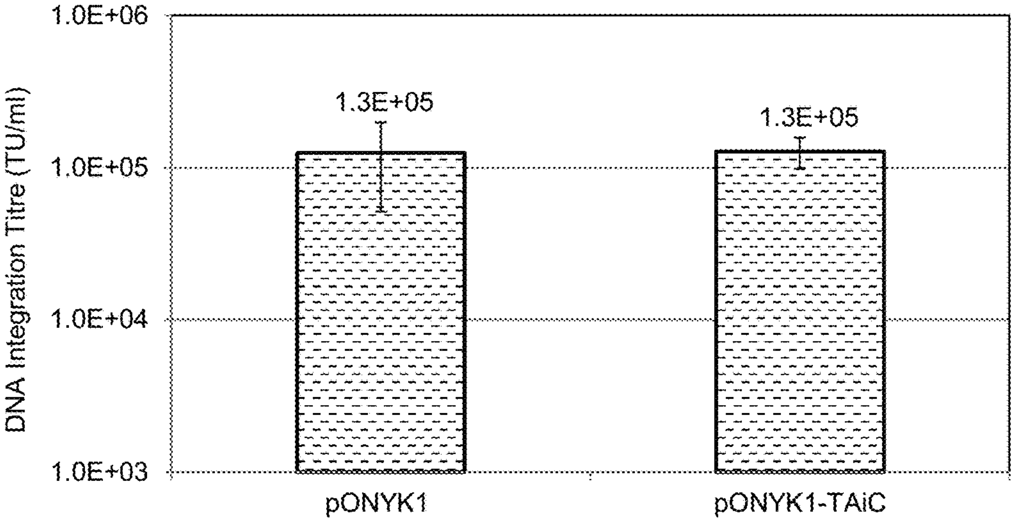
FIGS. 2*a* and 2*b* show vector production from pONYK-TAiC and catecholamine production from the integrated vector in HEK293T cells.
Figure 2:
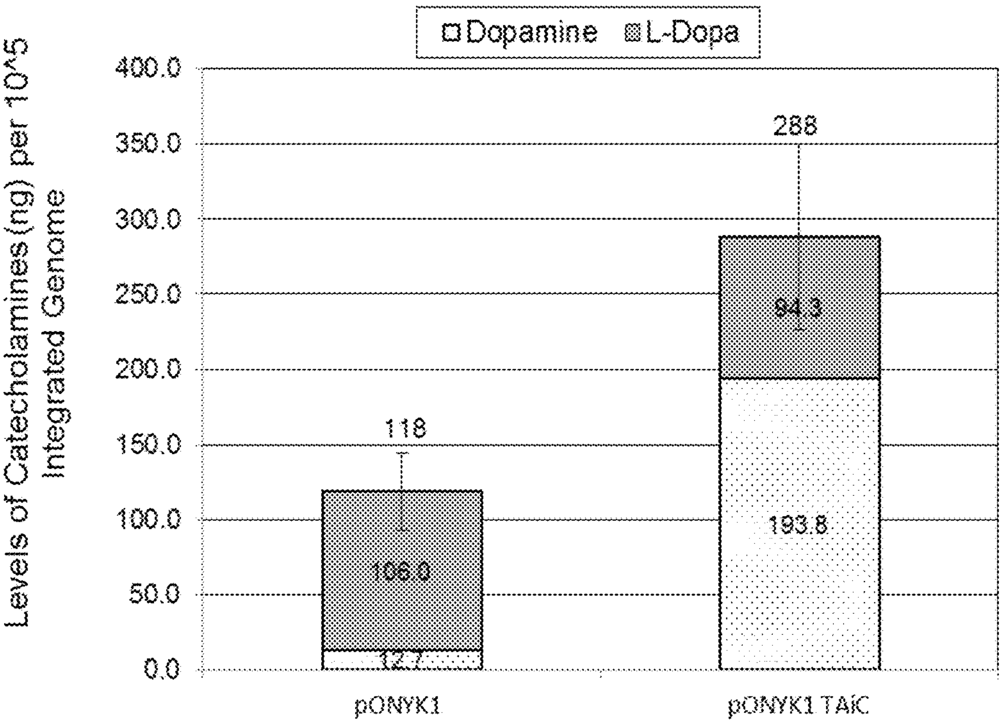

Example 1—Vector Production from pONYK-TAiC and Catecholamine Production from the Integrated Vector The first fusion construct to be generated and tested with a view to improving titre compared to pONYK1 was pONYK-TAiC (FIG. 1). Lentiviral vector (LV) preparations using the pONYK-TAiC or pONYK1 genomes were generated in triplicate and the resulting vector titres were quantified by DNA integration assay (FIG. 2*a*). These data surprisingly demonstrated that the titres of vector generated from pONYK-TAiC were the same as pONYK1; that is removal of one IRES element did not improve titre. HPLC analysis was performed on the transduced HEK293T cell supernatants to examine the levels of L-DOPA and dopamine produced. The HPLC results (FIG. 2*b*) demonstrated that cells transduced with pONYK-TAiC vector produced a 2.4 fold increase in the levels of total catecholamines compared to cells transduced with pONYK1 vector. L-DOPA levels were comparable between both genomes, however, the levels of dopamine were 15.3 fold higher for pONYK-TAiC than pONYK1. Thus catecholamine production was improved. Overall this implies that the dopamine biosynthetic pathway is more efficient when cells are transduced with pONYK-TAiC vector compared to the pONYK1 vector.

Figure 3:
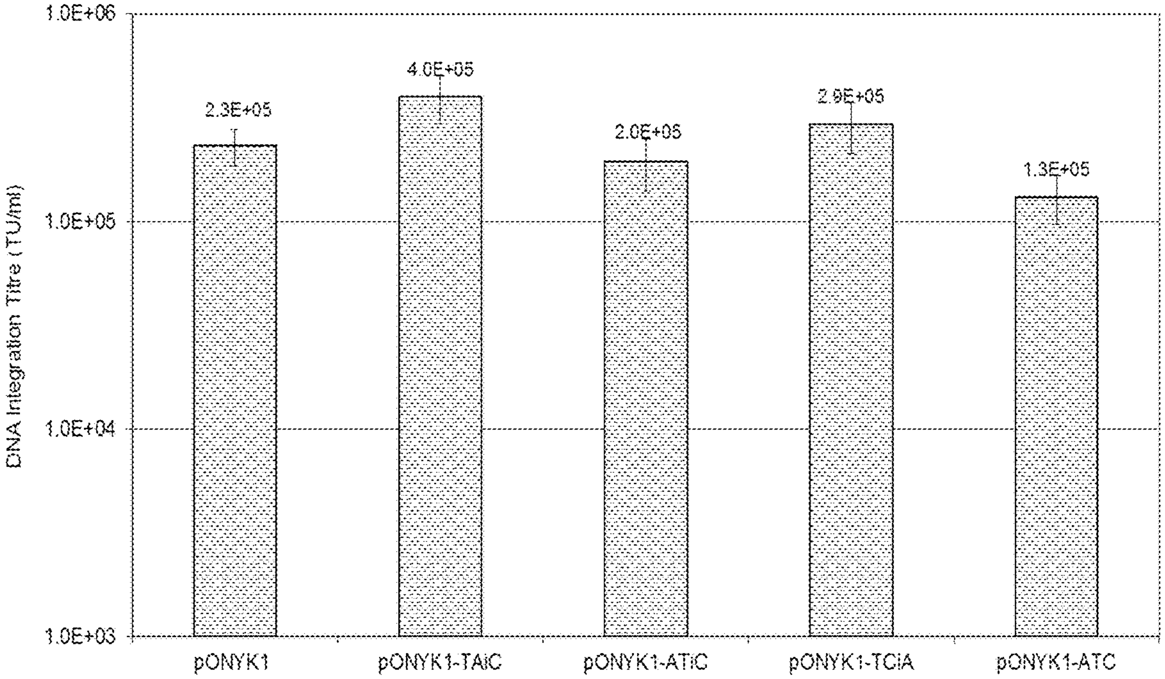
FIGS. 3*a* and 3*b* show vector and catecholamine production.
Figure 3:
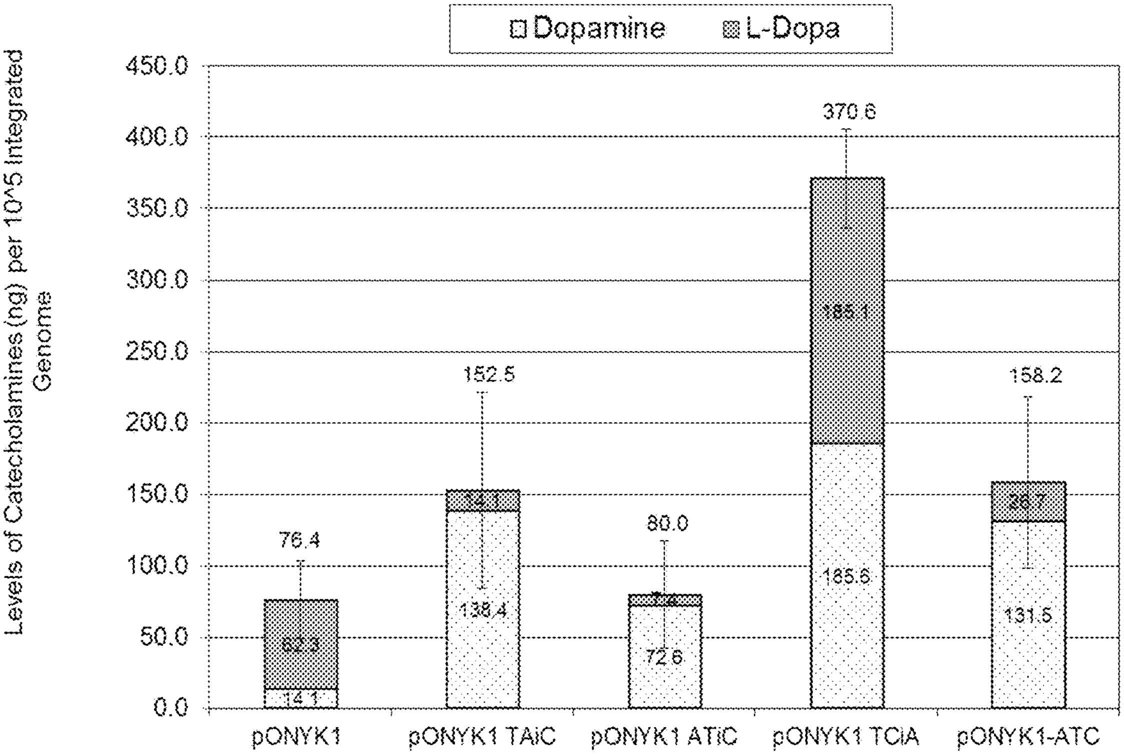

Example 2—Vector Production and Catecholamine Production from Integrated Vectors Another three dopamine enzyme fusion plasmids were tested (pONYK-ATiC, pONYK-TCiA, pONYK-ATC (FIG. 1) alongside pONYK-TAiC and pONYK1. LV preparations using each of the different genome plasmids were generated in triplicate and the resulting vector was quantified by DNA integration assay (FIG. 3*a*). The results demonstrated that the titres were similar for all the vectors, with titres ranging from 1.3E+05 TU/ml to 4.0E+05 TU/ml. Interestingly, pONYK-ATC which lacked both IRES elements did not show an increase in titre. This suggests that the fusion constructs do not alter vector production and rearrangement of the transgenes and presence of the GS15 linker(s) do not affect titres. The results from the HPLC analysis demonstrated that HEK293T cells transduced with each of the different vectors led to different catecholamine production (FIG. 3*b*). Furthermore, the amount of L-DOPA converted to dopamine varied significantly between the different vectors. The pONYK1 vector demonstrated the lowest levels of dopamine production and the lowest conversion of L-DOPA to dopamine. Vector generated using pONYK-TCiA demonstrated the highest catecholamine production (4.8 fold higher than pONYK1), with dopamine levels being 13.2 fold higher than pONYK1.

Thus, it appears when TH and CH1 is expressed as a single unit the highest levels of catecholamines are produced. Interestingly fusing all three genes together to yield a triple fusion construct (pONYK-ATC), resulting in one protein, demonstrated that dopamine production was increased (9.3-fold) when compared to pONYK1.

Figure 4:
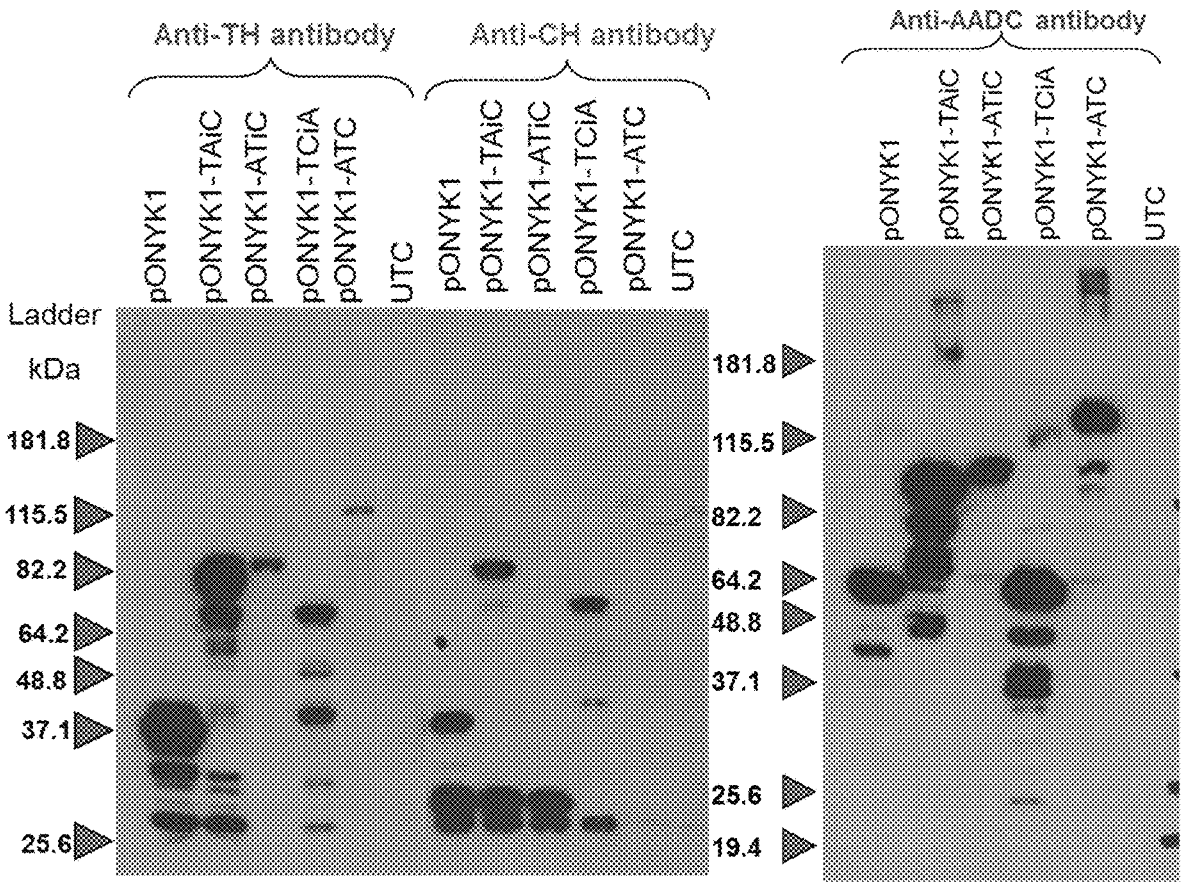
FIG. 4 shows detection of proteins in the dopaminergic pathway by western blot analysis.

Example 3—Assessing the Dopamine Enzyme Levels in HEK293T Cells Transfected with Different Fusion Plasmids To investigate protein expression levels, western blot analyses for each of the transgene products (AADC, CH1 and TH) was performed from cell lysates of HEK293T cells that had been transfected with each of the fusion genome plasmids (FIG. 4). Results demonstrated that for each of the different fusion constructs, each of the dopamine synthesising enzymes were present and of the predicted size. This demonstrated that each of the genome constructs was capable of expressing the dopamine synthesising enzymes with GS15 linkers, including the triple fusion cassette (pONYK-ATC), as a band of 124 kDa was seen in all three western blots; this is the expected size for a fusion protein containing all three linked dopamine enzyme proteins. The levels of each of the different proteins expressed by the different genomes constructs vary considerably. The highest levels of all three proteins appear to have been expressed from pONYK1, pONYK-TAiC and pONYK-TCiA. The lowest levels of proteins were seen from pONYK-ATC.

There does not appear to be a direct relationship between the intensities of the proteins on the western blots and the HPLC results. pONYK1 demonstrated one of the highest levels of protein expression, yet HEK293T cells transduced with vector made from this plasmid demonstrated the lowest dopamine production.

Example 4—Vector and Catecholamine Production from 5 Five Fusion Constructs

As discussed above, it appears that when TH and CH1 are expressed as a single unit the highest levels of catecholamines are produced. Since the levels of L-DOPA were very high with the pONYK-TCiA it is likely that expression levels of AADC are limiting L-DOPA to dopamine conversion. Since it is known that gene expression is reduced when the gene is placed after an IRES sequence, reversing the orientation of this configuration might result in maximal dopamine levels by increasing the conversion of L-DOPA to dopamine, thus the AADC gene is placed first in the expression cassette (downstream of the CMV promoter to maximise its expression followed by an IRES and then the TH:CH1 fusion). Thus, this genome construct (pONYK-ATC, FIG. 1) was generated. The western blot results from cells transfected with pONYK-ATC demonstrated low levels of the large fusion protein (Example 3). However, despite these apparent low levels, cells that were transduced with vector made from pONYK-ATC displayed high levels of conversion of L-DOPA to dopamine which resulted in high level dopamine production. This is surprising given that all three coding sequences are linked together which yields a large protein (124 kDa) that was relatively poorly expressed. Given that vector generated using pONYK-TCiA demonstrated the highest levels of dopamine production, and the known fact that IRES sequences reduce gene expression, it could be that a triple fusion of the transgenes placed in this same order (TH:CH1:AADC) will lead to an enhanced level of dopamine production from transduced cells. Therefore, a further triple fusion construct, pONYK-TCA (FIG. 1), was generated.

Figure 5:
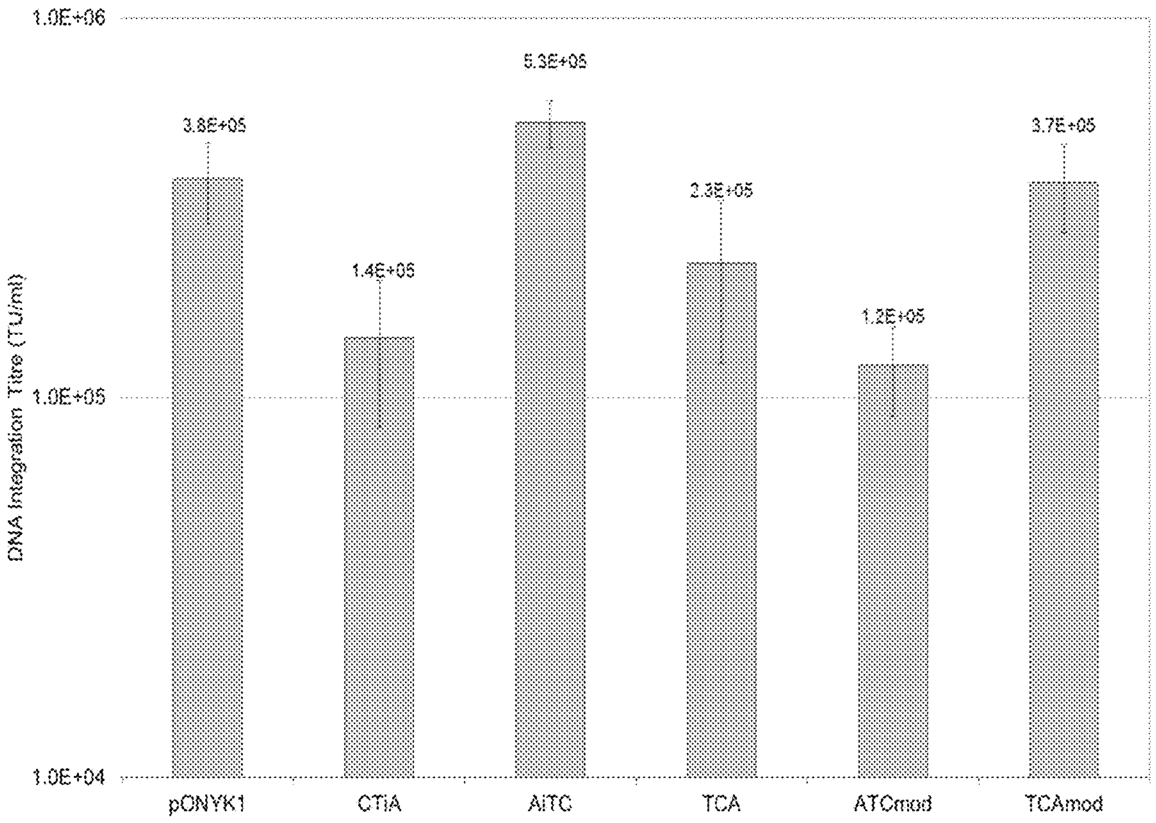
FIGS. 5*a* and 5*b* show vector and catecholamine production from five fusion constructs.
Figure 5:
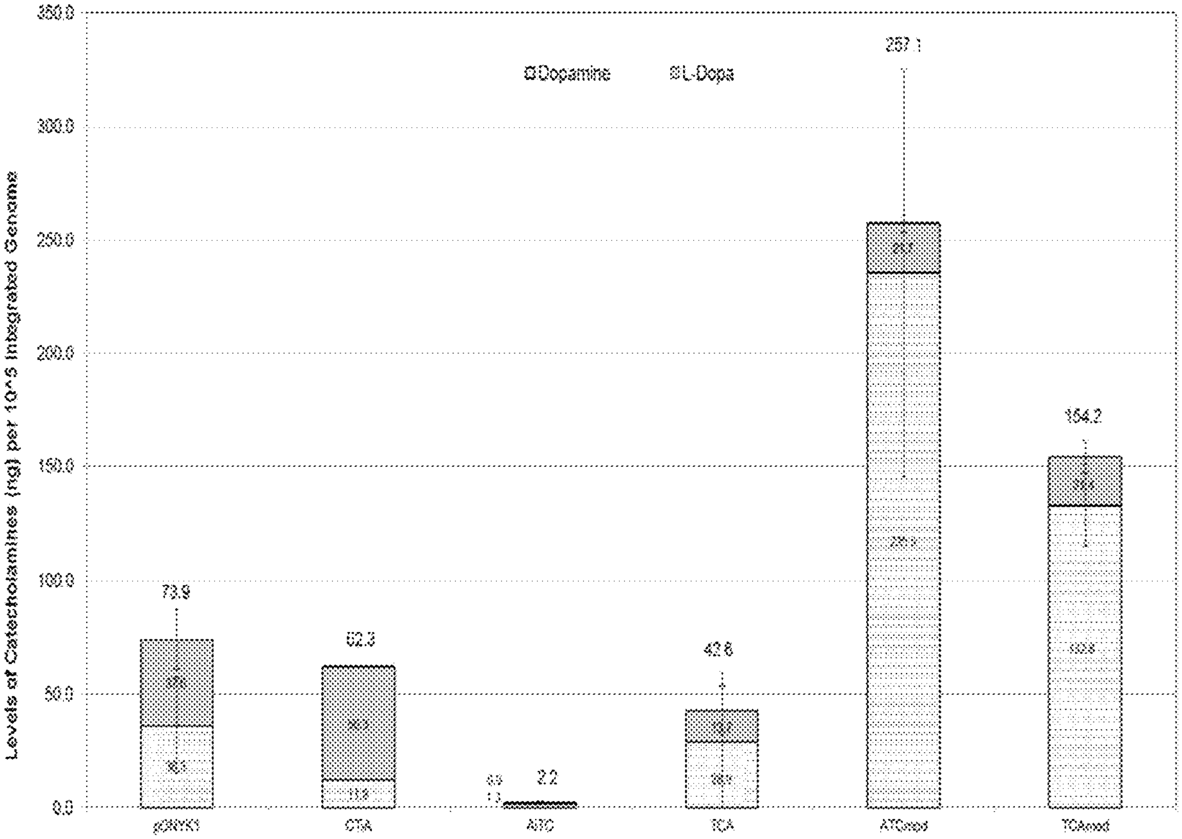

A modified GS15 linker was generated in which the amino acid sequence remained unchanged while the DNA sequence was altered. This linker was cloned into pONYK-ATC and pONYK-TCA replacing the original GS15 linker between the TH and CH1 genes. This yielded pONYK-ATCmod and pONYK-TCAmod (FIG. 1). Vector using each of the different genome plasmids was generated in duplicate and the resulting vector was quantified by DNA integration assay (FIG. 5).

As can be seen from the results, the vector titres for all constructs were similar with titres ranging from 1.2E+05 TU/ml to 5.3E+05 TU/ml. Thus, the new constructs do not alter vector production, so rearrangement of the transgenes and presence of the GS15 linker and/or the modified GS15 linker does not affect titre.

Catecholamine production from transduced HEK293T cells was performed by HPLC analysis and results are shown in FIG. **5*b***. The vectors that were generated from the new modified triple fusion constructs (ATCmod and TCAmod) demonstrated a further increase in catecholamine levels. The levels of dopamine production from cells transduced with both triple fusion constructs were much greater than the levels of L-DOPA, suggesting that the conversion of L-DOPA to dopamine was very efficient with these constructs. ATCmod vector transduced cells demonstrated the highest levels of catecholamine production with an overall 6.5 fold increase in dopamine production compared to pONYK1 transduced cells. Of further significance was the finding that dopamine levels produced from cells transduced with vector generated from the modified triple fusion constructs (using the modified linker between TH and CH1) were much greater than those produced from vector generated using the triple fusion genomes where both GS15 linkers had identical nucleotide sequences.

Figure 6:
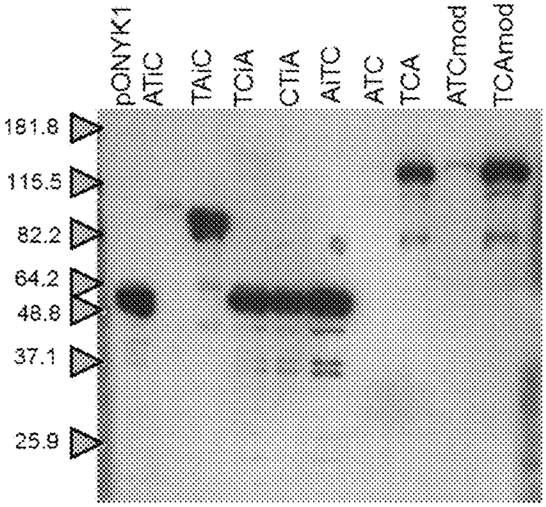
FIGS. 6*a*-6*c* show detection of proteins in the dopaminergic pathway by western blot analysis.

Example 5—Assessing the Dopamine Enzyme Levels in HEK293T Cells Transfected with Nine Different Fusion Plasmids To examine protein expression levels for each vector genome, western blot analysis for each of the transgene products (AADC, CH1 and TH) was performed using cell lysates from HEK293T cells that had been transfected with each of the vector genomes (FIG. 6). Results demonstrated that for all of the vector genomes, each of the dopamine synthesising enzymes was present and of the predicted size, depending on whether the enzyme was expressed as a fusion. This was of most importance for the new constructs which had not been previously tested (pONYK1-CTiA, pONYK1-AiTC, pONYK1-TCA. pONYK1-ATCmod and pONYK1-TCAmod). This demonstrated that each of the genome constructs were capable of expressing the dopamine synthesising enzymes with GS15 linkers. This included the triple fusion cassettes (TCA and ATC) where a protein band of the expected size (124 kDa) was seen in all three western blots.

The highest levels of all three proteins appear to have been expressed from pONYK1, pONYK1-TAiC and pONYK1-TCAmod (FIG. 5). The lowest levels of proteins were seen from pONYK1-ATC which is comparable to previous results (FIG. 4).

Figure 8:
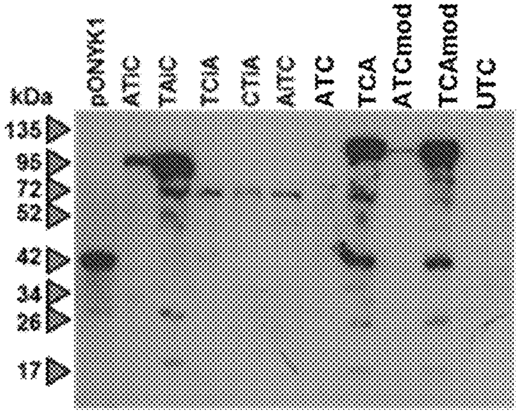
FIGS. 8*a*-8*c* show detection of proteins in the dopaminergic pathway from HEK293T transduced cells by western blot analysis.
Figure 8:
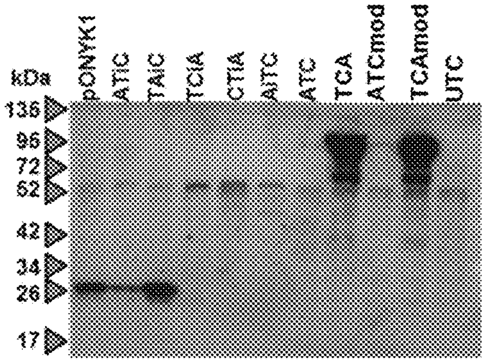
Figure 8:
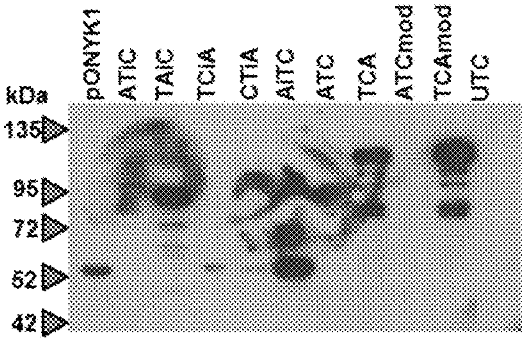

Example 6—Assessing the Dopamine Enzyme Levels in HEK293T Cells Transduced with Nine Different Fusion Vectors As described above, western analysis was performed on cell lysates from cells transfected with the fusion plasmids (FIGS. 4 and 6). This was followed by analysis of dopamine synthesising enzyme levels from cells transduced with each of the fusion vectors. Analysis of protein levels from transduced cells gives a better insight into the levels of proteins expressed from resulting functional vector. HEK293T cells that had been transduced with each of the fusion constructs were analysed by western blotting for protein expression of each of the dopamine synthesising enzymes and results are shown in FIG. 8. The blots demonstrated that the correctly sized protein was expressed for each vector genome cassette. The data suggested that protein levels are reduced when a coding sequence has been placed downstream of the IRES element.

Cells transduced with vector generated using the modified linker in the triple fusion constructs (ATCmod and TCAmod) demonstrated higher levels of dopamine production when compared to cells transduced with vector generated from the constructs with the unmodified linker (ATC and TCA) (FIGS. 3*b* and 5*b*).

Example 7—Transduction of Rat Striatal Neurons with Fusion Constructs

Figure 9:
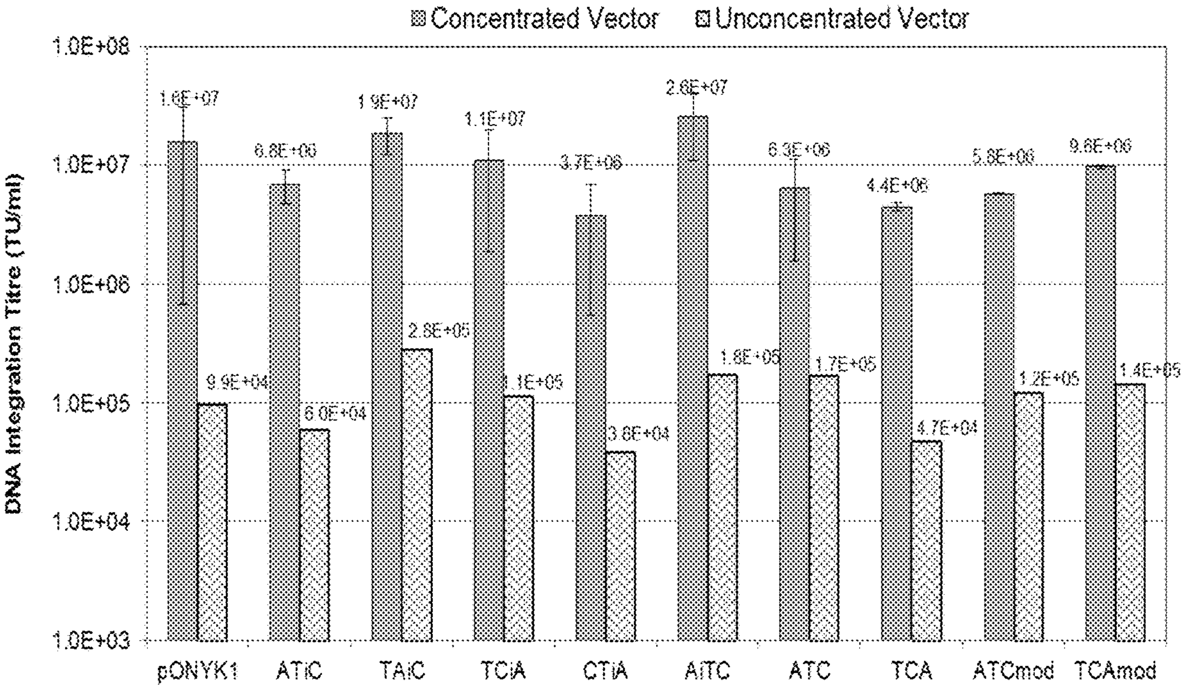
FIG. 9 shows results from DNA integration assay to assess vector titre of unconcentrated and concentrated fusion vector preparations.

It was decided to transduce rat striatal neurons, the target cell population for dopamine replacement therapy, with each of the fusion vectors and to assess catecholamine production from these primary cells. A preliminary experiment was performed using an EIAV-GFP vector to establish the optimal transduction conditions for neurons (data not shown). Vector manufacture was performed using each of the vector genomes previously described and the unconcentrated vector supernatants and concentrated final vector was quantified by DNA integration assay (FIG. 9). The concentrated vector preparations were used to transduce the striatal neurons at an MOI 1 and in triplicate. In parallel, striatal neurons were transduced with an EIAV-GFP vector at an MOI 1. This was performed to act as a control for transduction as visualisation of transduction can be easily observed by the presence of GFP positive cells, and also as negative control for the HPLC analysis. As seen from FIG. 10*a* the neuronal cells were successfully transduced with EIAV-GFP at an MOI 1.

Figure 10:
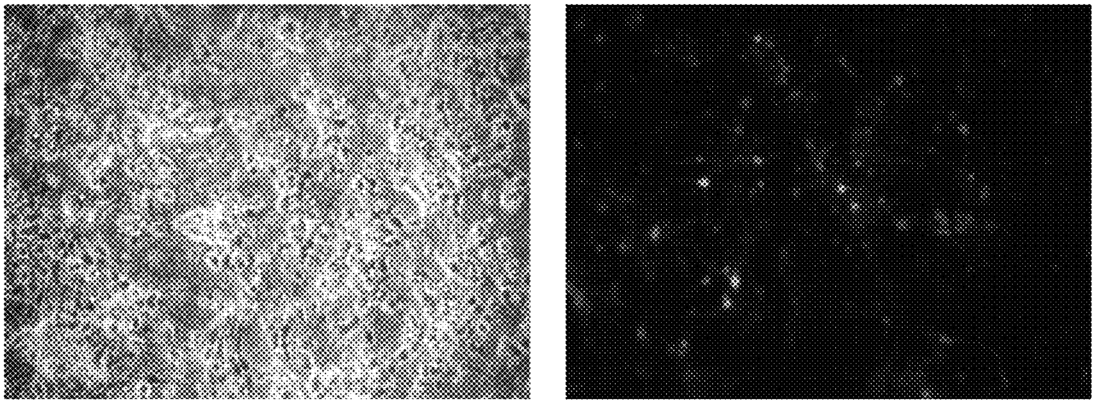
FIGS. 10*a* and 10*b* show striatal neurons transduced with EIAV vector at an MOI 1.
Figure 10:
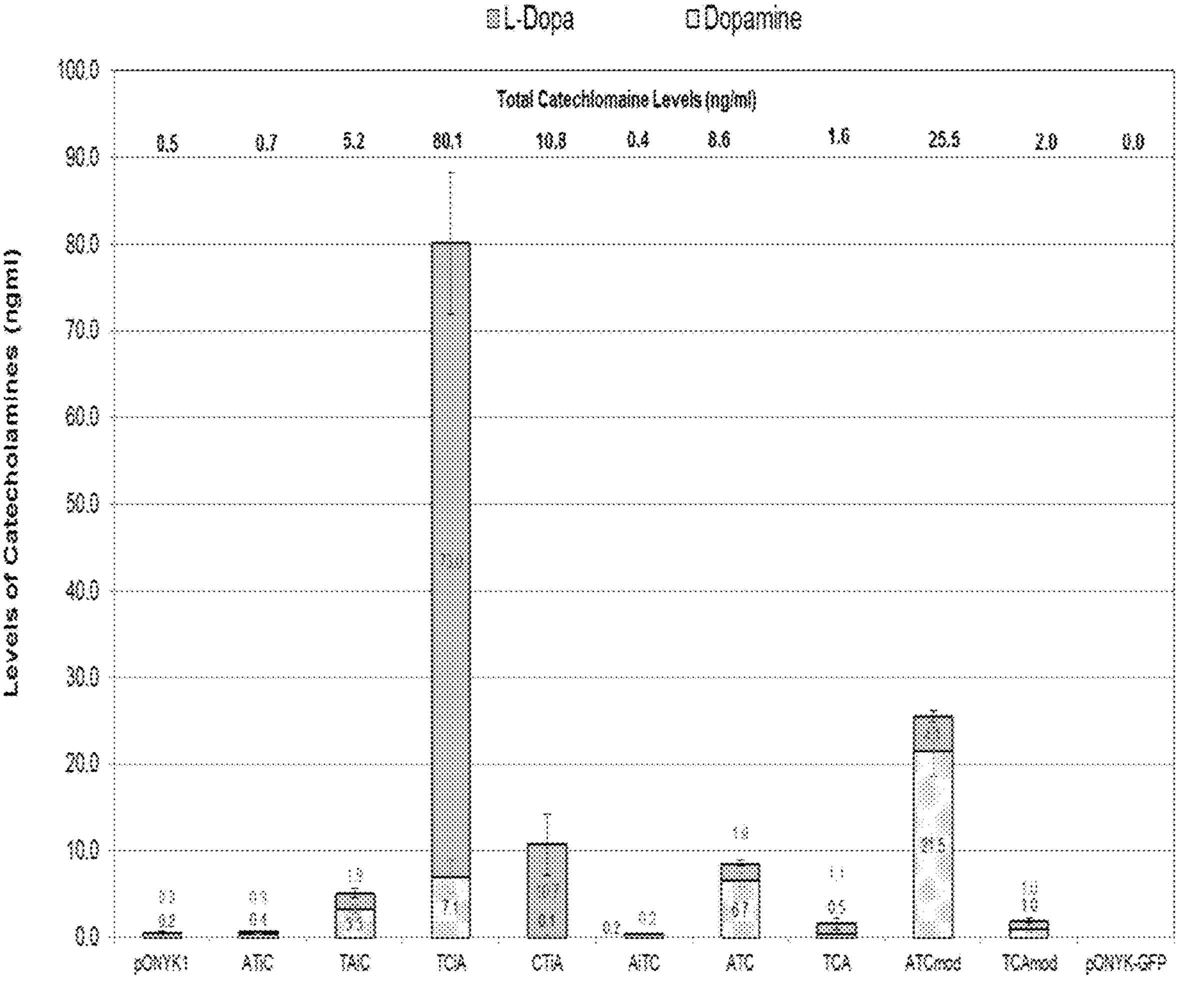

HPLC analysis demonstrated that transduction using an MOI 1 was sufficient to allow detection of dopamine and L-DOPA levels in the striatal cultures (FIG. 10*b*). FIG. 10*b* demonstrates that neurons transduced with TCiA vector demonstrated the greatest production of catecholamines (80 ng/ml) which was 160-fold higher than neurons that had been transduced with pONYK1 vector. However, most of the detected catecholamines (73 ng/ml) were L-DOPA and not dopamine. The conversion of L-DOPA to dopamine from TCiA was therefore inefficient. The inefficient conversion of L-DOPA to dopamine observed from TCiA transduced cells is a result that has been observed in all experiments to date (FIGS. 3*b*, 5*b*, 6*b* and 10*b*). As previously discussed, this is almost certainly due to restricted expression of AADC. For TCiA vector to work more efficiently, in terms of dopamine production, expression levels of AADC would need to be increased. However, placing AADC before the IRES TH-CH1 fusion construct (AiTC) did not provide a solution as catecholamine levels from neurons transduced with this vector were low (FIG. 10*b*), presumably due to low L-DOPA levels from placing TH-CH1 after the IRES. Fusing all three transgenes together with AADC first in the configuration did improve the conversion of L-DOPA to dopamine (see results for ATC and ATCmod transduced neurons), but the overall catecholamine production was lower compared to TCiA. Nonetheless the dopamine levels achieved with this vector genome (21.5 mg/ml) were the highest of all the constructs evaluated. This represents a 107.5-fold increase in dopamine levels compared to neurons transduced with pONYK1.

The dopamine to L-DOPA ratio from neurons transduced with ATCmod was extremely high (5.2) indicating nearly total conversion of L-DOPA to dopamine. This efficient conversion of L-DOPA to dopamine was also observed in neurons transduced with ATC vector but the total catecholamine production was lower. This result was previously observed from ATC and ATCmod vector transduced HEK293T cells (FIGS. 3*b* and 5*b*) and confirms that the addition of the modified linker (GS15mod) into ATCmod confers higher catecholamine production.

Example 8—Evaluation of TCiAmod

Figure 11:
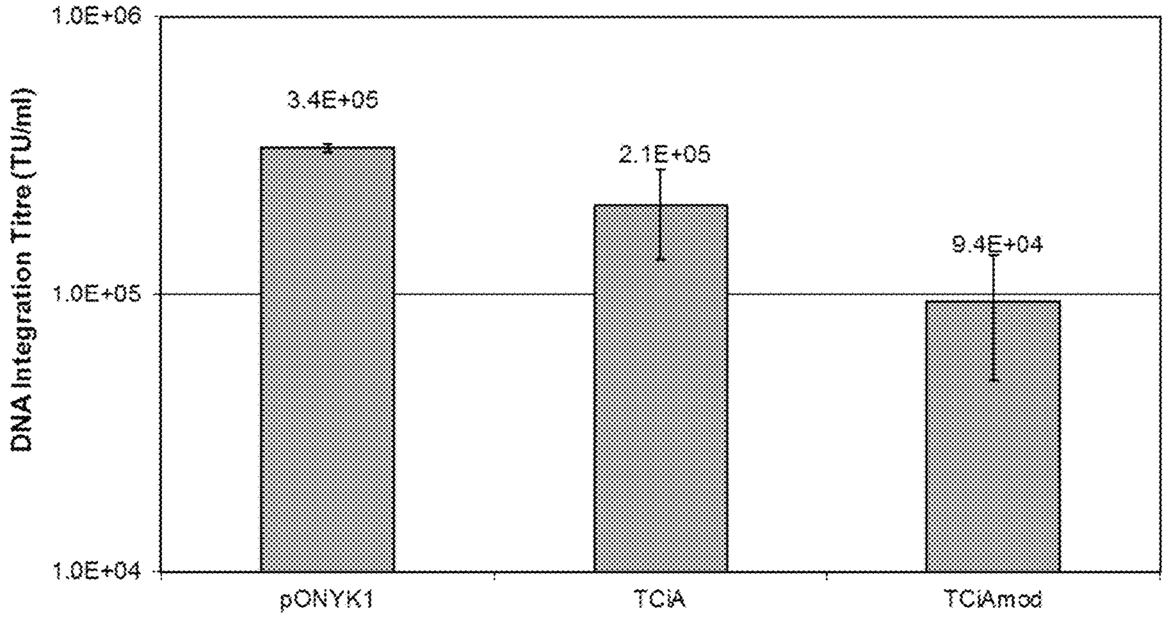
FIGS. 11*a* and 11*b* show vector production from TCiAmod and catecholamine production from the integrated vector.
Figure 11:
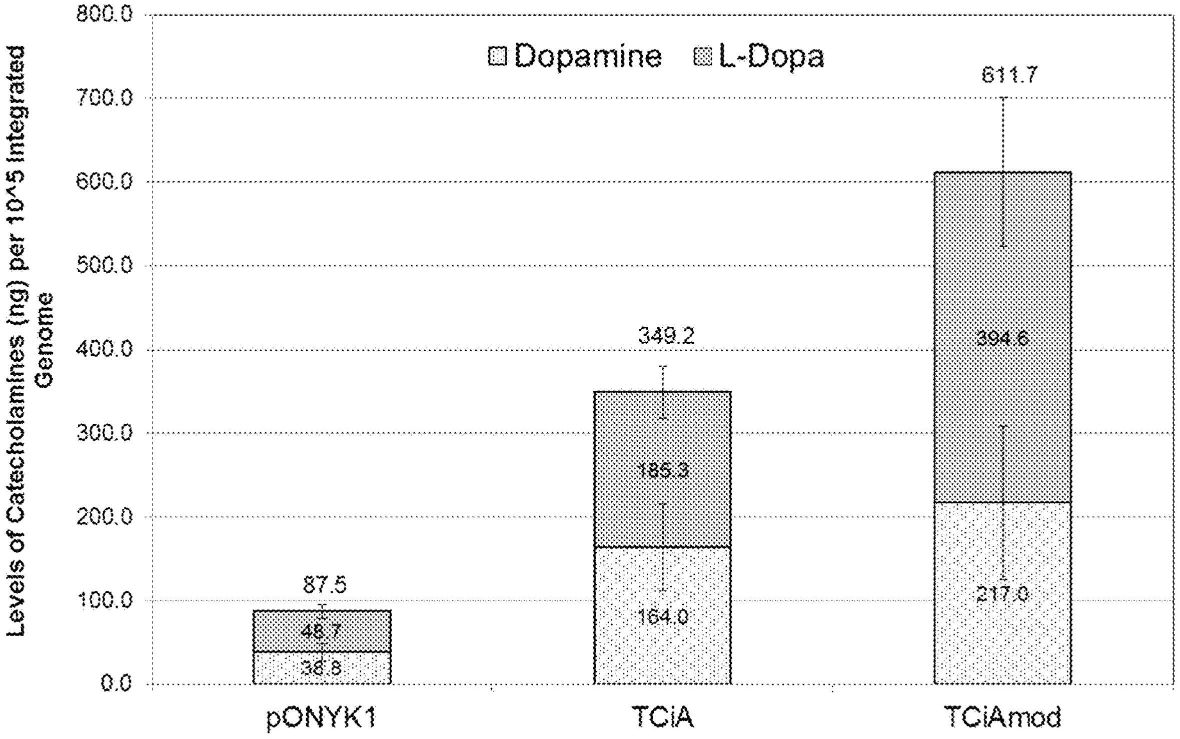

As discussed, the modified GS15 linker (GS15mod) used to link TH and CH1 in the ATCmod and TCAmod triple fusion genomes has demonstrated higher dopamine production from cells (neurons and HEK293T) transduced with vector made from these constructs than from cells transduced with vector generated from the parental genomes (which contain identical GS15 linkers). It was decided to establish if this modified GS15 linker would lead to the increase of catecholamine production from vector made from a single fusion genome. As the highest catecholamine production has been observed from TCiA vector transduced cells, it was decided to replace the unmodified GS15 linker in TCiA with the modified linker to yield TCiAmod (FIG. 1). As seen in FIG. 11*a*, vector titres from TCiAmod versus pONYK1 and TCiA were lower (3.4-fold and 2.2-fold lower, respectively) but this was likely to be caused by vector production and assay variation.

Determination of catecholamine production from the transduced HEK293T cells was performed by HPLC analysis and results are shown in FIG. 11*b*. TCiAmod vector transduced cells demonstrated a 7-fold increase in catecholamine production when compared to cells transduced with the pONYK1 genome. Furthermore, catecholamine production from TCiAmod vector transduced cells was increased by 1.75-fold when compared to cells transduced with TCiA vector. This confirms that the GS15mod linker provides an advantage over than the unmodified GS15 linker, and this phenomenon is not just related to the triple fusion constructs.

As reported, TCiA has previously demonstrated high catecholamine production but the relative amounts of dopamine and L-DOPA are comparable, indicating that the conversion of L-DOPA to dopamine by AADC is limiting. This trend was also evident with TCiAmod, presumably since AADC is still expressed downstream of the IRES and hence unaffected by the change in linker.

SUMMARY

Ten fusion genomes expressing AADC, CH1 and TH have been constructed. Five contain the GS15 linker in place of one of the IRES elements (TCiA, TAiC, ATiC, CTiA and AiTC). The remaining four constructs are triple fusion constructs in that GS15 linkers have replaced both IRES elements. Two of these constructs contain identical GS15 linkers (ATC and TCA) while the other two triple constructs contain the same gene arrangement but with a modified linker (GS15mod) placed between TH and CH1 genes (ATCmod and TCAmod). This GS15mod linker encodes the same amino acid sequence but has a different DNA sequence to the original GS15 linker. The GS15mod linker was also inserted into TCiA replacing the unmodified linker to yield TCiAmod.

These studies tested the hypothesis that removal of the IRES elements from the pONYK1 tricistronic genome and replacement with linker sequences may improve vector titres by eliminating the complex structures contained within the IRES elements that were thought to impede efficient reverse transcription. This theory was disproved as vector titres from the different fusion genomes gave similar titres to pONYK1. Titres within assays did vary, but comparison of all assays did not identify a fusion vector that consistently gave the lowest titres suggesting that no specific fusion genome conferred low vector production.

Western blot analyses (FIGS. 4 and 8) demonstrated that each of the catecholaminergic enzymes were expressed and of the correct predicted size for each of the different fusion constructs. It was also suggested from the western analysis that protein levels were reduced when transgenes were placed downstream of an IRES element.

Unexpectedly, evaluation of the constructs demonstrated that fusion of TH and CH1 provided the best mechanism for increasing total catecholamine production, presumably due to efficient catalysis of tyrosine to L-DOPA by this TH:CH1 fusion.

Construction of triple fusion genomes (ATC and TCA), using two copies of the GS15 linker, did not compromise vector production and increased catecholamine production compared to pONKY1.

The use of a modified GS15 linker (GS15mod) between the TH and CH1 genes also resulted in an increase in catecholamine production with both constructs despite no evidence for an increase in protein expression. The increased efficiency of the modified linker to mediate increased catecholamines was also demonstrated when applied to the TCiA configuration (TCiAmod).

Overall the data suggest that the TCiAmod and ATCmod genomes are both capable of mediating improved dopamine production compared with PONYK1. TCiAmod generally mediates the highest combined levels of L-DOPA and dopamine, whereas ATCmod generally mediates the highest levels of dopamine.

Example 9—Replacement of the IRES with a Constitutive Promoter

Since dopamine production using the TCiAmod configuration is limited by IRES-mediated AADC expression, replacing the IRES with a constitutive promoter may result in increased ADDC expression and enable higher levels of dopamine production in transduced cells. Two alternative genomes were therefore created that replace the IRES element in TCiAmod with either the PGK or TK promoter (see FIG. 1).

Example 10—Transduction of Primary Cortical Neurons

Figure 12:
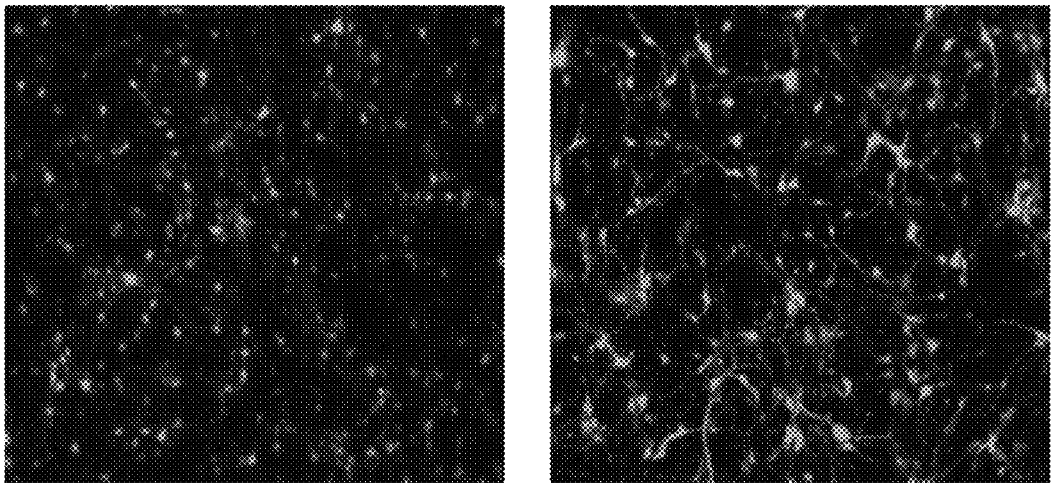
FIGS. 12*a* and 12*b* show transduction of human primary cortical neurons with pONYK1, fusion and GFP vectors.
Figure 12:
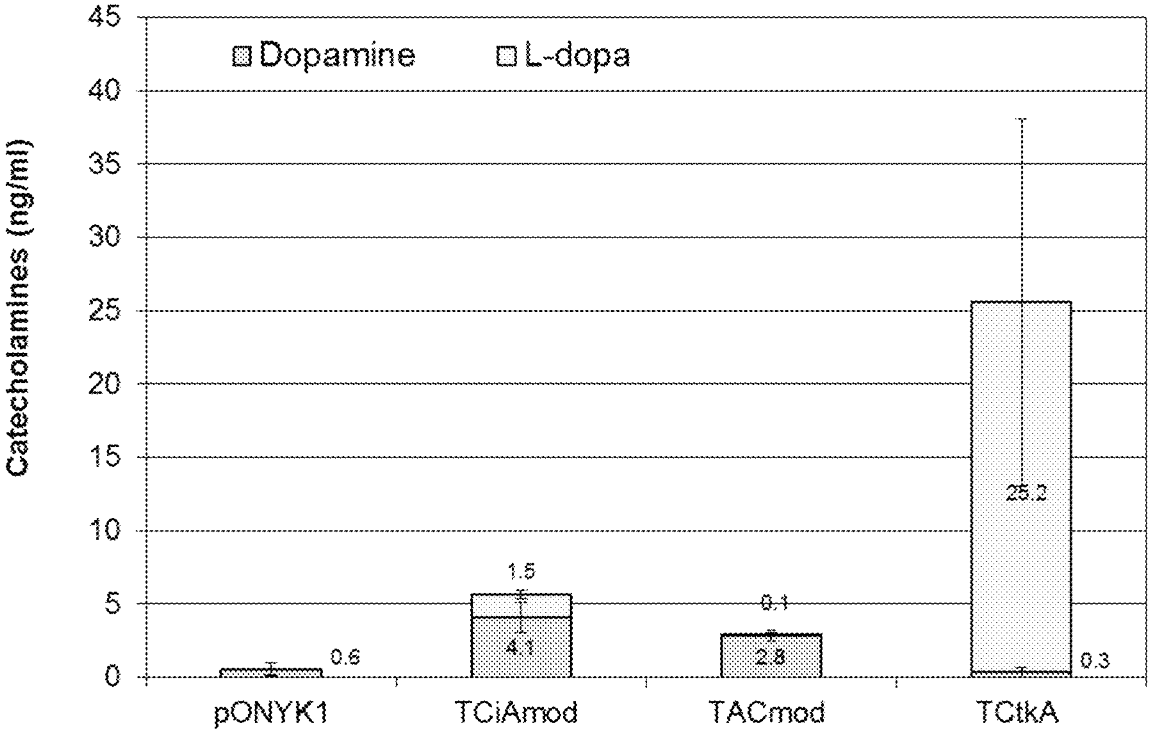

Three fusion vectors (TACmod, TCiAmod and TCtkA) and were used to transduce human primary cortical neurons (Innoprot, Catalogue number P10151) in triplicate at an MOI of 0.4. These vectors had similar titres to pONYK1 (pONYK1 1.5E+08 TU/ml, TACmod 7.4E+07 TU/ml, TCiAmod 8.4E+07 TU/ml, TCtkA 1.2E+08 TU/ml) As a control, GFP vector was used to transduce the human neurons at MOIs 2 and 10. To ensure transduction had occurred GFP transduced cells were assessed for GFP florescence and at the end of the study (9 days post transduction) images were captured and are shown in FIG. 12*a*. A high percentage of GFP fluorescent cells were visualised at both MOIs 2 and 10 indicating that transduction with GFP vector at both MOIs had been successful. Cell supernatants were harvested for catecholamine HPLC analysis 5 days (harvest 1) and 9 days (harvest 2) post transduction. Results from the HPLC analysis at harvest 1 are shown in FIG. 12*b*. HPLC data from harvest 2 were comparable to those seen from harvest 1 (data not shown).

Cells transduced with TCtkA showed significant production of L-DOPA (>25-fold higher than pONYK1) yet low dopamine production (lower than pONYK1), suggesting inefficient conversion of L-DOPA to dopamine.

The highest level of dopamine production was observed from cells transduced with TCiAmod which demonstrated a 7.4-fold improvement in dopamine production compared to those transduced with pONYK1. Furthermore, L-DOPA levels were not in excess of dopamine production suggesting efficient conversion of L-DOPA to dopamine.

Figure 13:
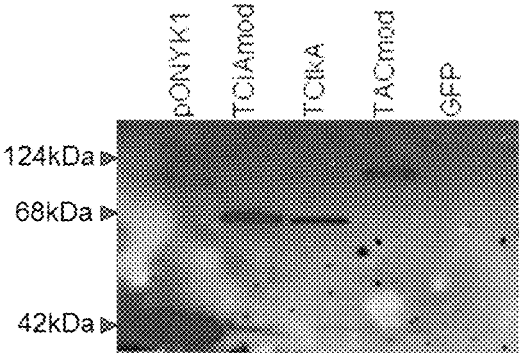
FIGS. 13*a* and 13*b* show detection of dopamine synthesising enzymes from transduced human cortical neurons by western blot analysis.
Figure 13:
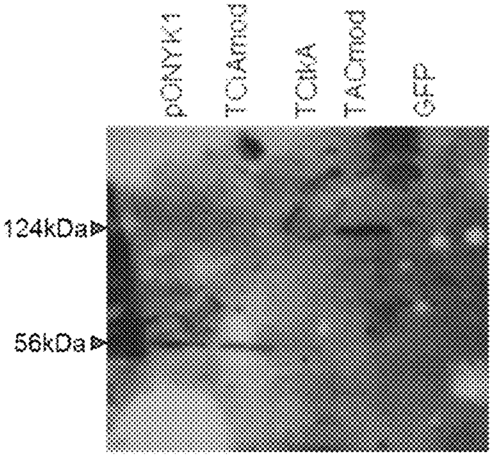

In addition to the HPLC analysis, western blots were performed to assess the TH and AADC protein levels expressed from the human cortical neurons transduced with the different vectors. These results are shown in FIGS. 13*a* and *b*. The western blots demonstrated that the correct sized dopamine synthesising enzymes (TH, and AADC) were expressed from human neurons transduced with the different vectors.

Levels of AADC (FIG. 13*b*) could barely be detected from cells transduced with TCtkA which may explain the high L-DOPA:dopamine ratio for cells transduced with this construct as described above.

Example 11—Behavioural and PET Imaging Assessments of TCiA(Mod) and pONYK1 in a Non-Human Primate Model of Parkinson's Disease The aim of the study, which is underway, is to compare two dose levels of TCiA(mod) with a single dose level of pONYK1 on the behavioural recovery of MPTP-treated non-human primates; in addition $^{18}$F-FMT and $^{18}$F-Fallypride PET imaging is carried out on all stably parkinsonian animals before surgery and again at 3 months post injection to assess AADC or D2/D3 receptor levels respectively, healthy animals are used as a control to determine the normal baseline levels of each radiotracer.

Four groups, each of four MPTP lesioned m. fascicularis, are treated with viral vector as described below (MPTP lesioning and vector administration are detailed in Materials and Methods). Each group is followed for up to six months after administration of vector:

| | Group 1 | Group 2 | Group 3 | Group 4 |
|---|---|---|---|---|
| pONYK1 (full strength dose) | 2 animals | | 2 animals | |
| TCiA(mod) (full strength dose) | 2 animals | | 2 animals | |
| TCiA(mod) (⅕ dose) | | 2 animals | | 2 animals |
| LacZ | | 2 animals | | 2 animals |

The four animals from Group 1 receive baseline $^{18}$F-FMT and $^{18}$F-Fallypride PET scans. In addition, each animal from all groups undergo (see Materials and Methods for details):

1 MRI baseline scan 1 month of video-based characterisation of baseline locomotor activity (as assessed by Ethovision)

2 months of MPTP intoxication and video-based assessment of locomotor activity (Ethovision)

1 post-MPTP $^{18}$F-FMT PET scan 1 post-MPTP $^{18}F$-Fallypride PET scan 1 oral L-DOPA challenge and 1 oral control challenge as required each followed by Ethovision analysis (over 6 hours of film)

1 blood sample collected before virus administration 1 surgical procedure to deliver vector to the brain Behavioural follow-up (Ethovision), post-treatment for 3 months (0-3 months)

1 MRI scan at 3-months post-treatment

1 $^{18}F$-FMT PET scan at 3 months post-treatment

1 $^{18}F$-Fallypride PET scan at 3 months post-treatment 1 oral L-DOPA challenge and 1 oral control challenge as required each followed by Ethovision analysis (over 6 hours of film) at 3 months post-treatment Behavioural follow-up (Ethovision) post-treatment for additional 3 months (3-6 months)

1 blood sample collected before euthanasia.

Euthanasia (transcardial perfusion and brain extraction)

Post-mortem histological analysis including staining for: NeuN, GFAP, lbal, AADC, CH1 and TH or j3 gal.

Figure 14:
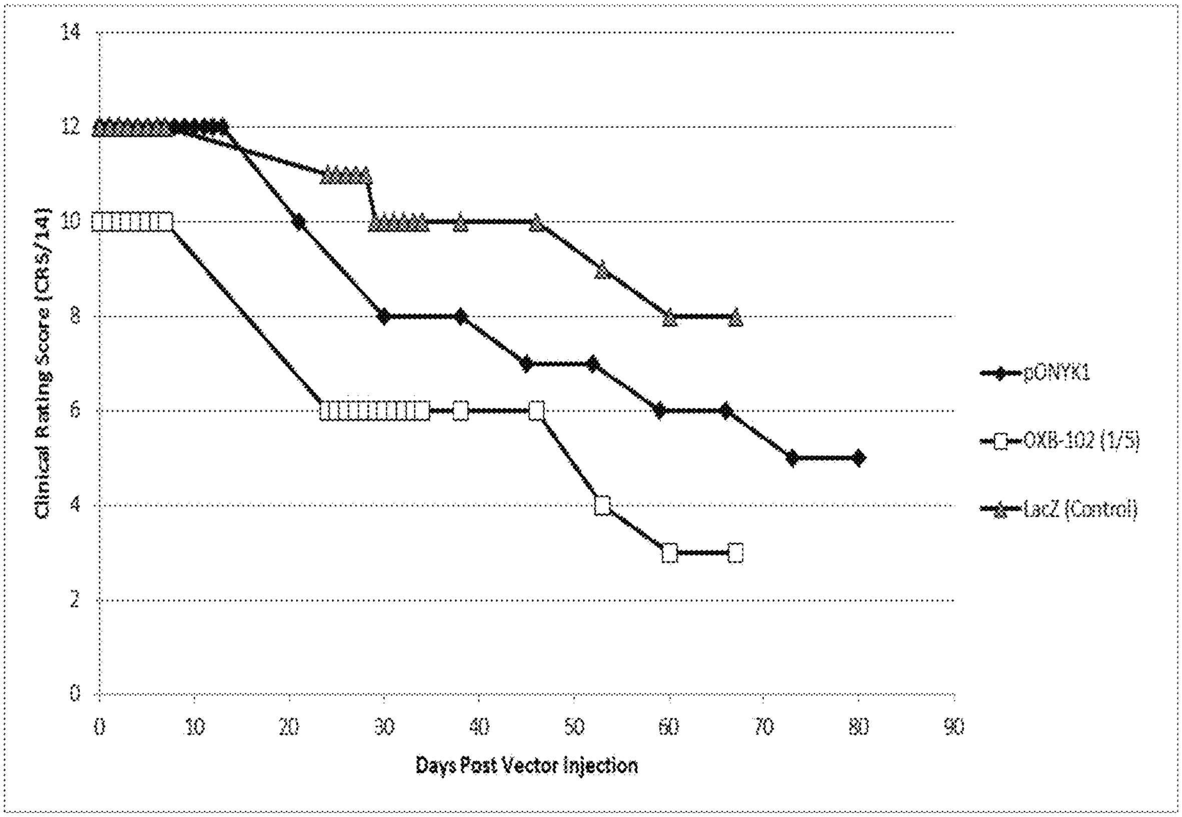
FIG. 14 is a graph showing the clinical rating scores (maximum 14) following stereotactic vector administration on Day 1.

FIG. 14 shows that the ⅕ dose of TCiA (OXB-102) is more effective than pONYK1 in improving the Parkinson's symptoms as assessed by the clinical rating score. The control EIAV-LacZ treated animal was still severely impaired by these timepoints.

Figure 15:
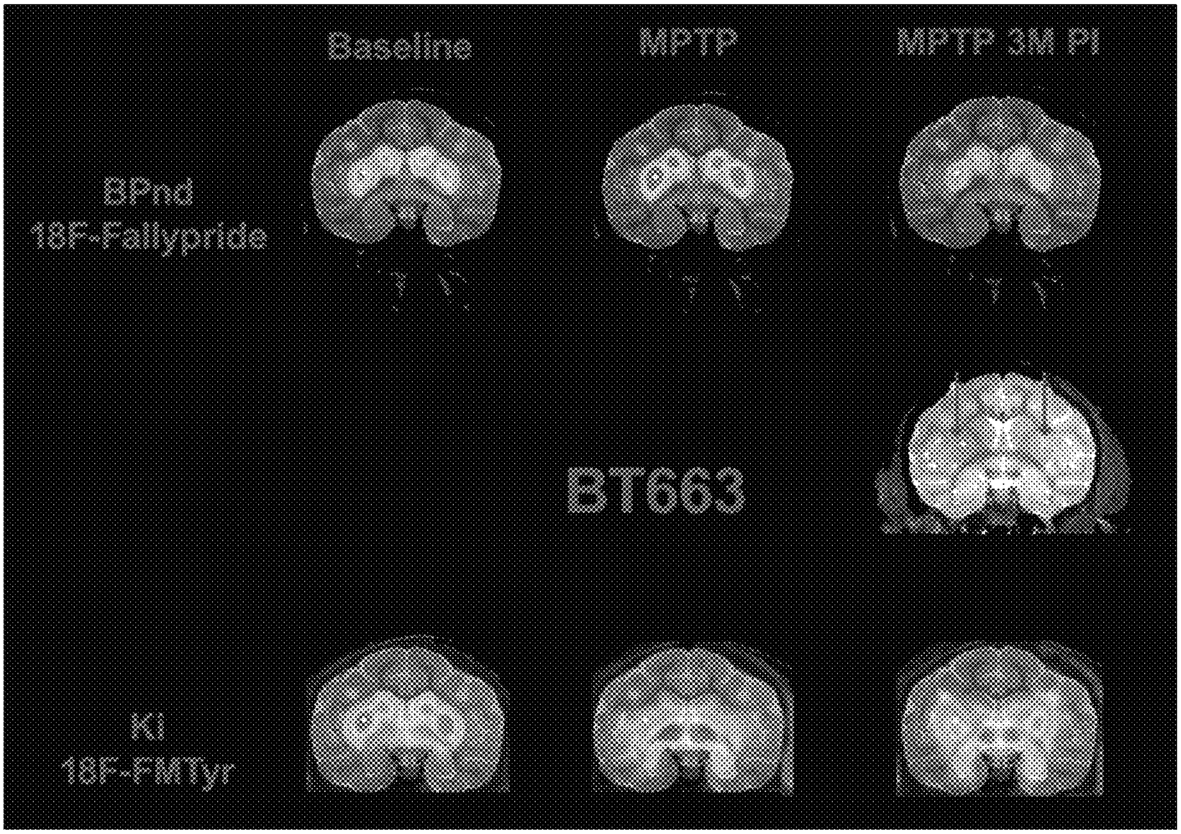
FIG. 15 shows PET images of a cynomolgus macaque brain at baseline (Baseline), following MPTP lesioning (MPTP) and finally 3 months after OXB-102 vector administration (MPTP 3M PI). The animal was treated, on separate occasions with radiotracers $^{18}$F-FMT (18F-FMTyr) and $^{18}$F-Fallypride (18F-Fallypride).

The Fallypride PET images of FIG. 15 show a relative increase in dopamine D2/D3 receptors following MPTP lesioning compared to baseline that decreases following treatment with the OXB-102 vector. The FMT PET images show a relative decrease in AADC expression in the putamen following MPTP lesioning compared to baseline that increases in the putamen following treatment with the OXB-102 vector.

Materials and Methods

Cell Lines

HEK293T cells used for transient transfection were obtained from M Calos (Stanford University). HEK293T cells were maintained in Dulbecco's modified Eagle's medium (DMEM) (Sigma, Poole, UK, Cat. D5671) containing 10% (v/v) foetal calf serum (FCS) obtained from PAA and supplemented with 2 mM L-Glutamine (Sigma, Cat. G7513) and 1% non-essential amino acids (Sigma, M7145).

Rat Striatal Neurons

The striatum was removed from Wistar rats (embryonic day 18) as described previously (Mazarakis et al., 2001) and *striata* were pooled and cultures prepared as described previously (Azzouz et al., 2002). The resulting cultures were plated into 24-well plates at a density of 7.5E+04 cells per well in 500 μl Neurobasal medium and maintained in a 37° C. incubator containing 5% $CO_2$.

Prior to transduction the media was removed from each well and combined and 250 μl added back to each well, this ensured that each well contained an equal volume of condition media. The required amount of vector to achieve an MOI 1 was added to each well in duplicate or triplicate. For the negative control two wells of striatal neurons were transduced with a GFP expressing vector at an MOI 1 (pONYK-GFP, Lot: KG120310). Three to six hours post-transduction 250 μl media was added to each well.

In order to measure catecholamine production neuronal cultures were cultured for 4 days post transduction when L-tyrosine was added to each well at a final concentration of 100 uM and cultures incubated overnight. The following morning 400 μl of neuronal culture supernatant was harvested and placed into tubes containing 40 μl of 2M Perchloric acid and 40 μl of Sodium Metabisulphite and samples were processed for catecholamine analysis by HPLC detection as discussed previously

Human Primary Cortical Neurons

Human cryo preserved neurons were obtained from Innoprot (Cat. P10151, Lot. 6195, 5E+06 cells/vial). A 24-well plate was poly-L-lysine (PLL) coated (Innoprot, Cat. PLL) at 2 ug/cm$^2$. The human neurons were defrosted and resuspended to a density of 1.2E+06 cells/ml in serum-free neuronal medium supplemented with neuronal growth supplement (NGS) and penicillin/streptomycin solution (Innoprot Cat. P60157). The diluted neuronal suspension was added to the centre of a well of the PLL coated plate at 6E+04 cells/well, in a total volume of 50 μl. The plate was incubated at 37° C. for 30 minutes to allow the neurons to attach, after which time the wells were flushed with 0.5 ml complete neuronal medium. Cells were incubated at 37° C. for 4 days before transduction. Prior to transduction the media was removed from each well and combined and 250 μl added to each well, this ensured that each well contained an equal volume of condition media. The required amount of vector to achieve an MOI 0.4 was added to each well in triplicate. As a control neurons were transduced with a GFP expressing vector at MOIs 2 and 10 (pONYK-GFP, Lot: KG290711). Three to six hours post-transduction 250 μl media was added to each well.

In order to measure catecholamine production neuronal cultures were cultured for 4 days post transduction when L-tyrosine was added to each well at a final concentration of 100 uM and cultures incubated overnight. The following morning 300 μl of neuronal culture supernatant was harvested and placed into tubes containing 30 μl of 2M Perchloric acid and 30 μl of Sodium Metabisulphite and samples were processed for catecholamine analysis by HPLC detection as discussed previously. The control neuronal samples that had been transduced with GFP vector were analysed for GFP florescence to ensure that transduction had occurred and images were captured and documented.

Plasmids

The minimal pONYK1 genome plasmid, has been more recently described as pONY8.9.4TY (containing the KanR gene) (Jarraya et al., 2009 Science Translational Medicine 1, 2ra4). This plasmid was based on pONY8.0T which is described in greater detail by Azzouz M et al (Azzouz et al., 2002 J Neurosci 22, 10302-10312). In brief, pONYK1 is an EIAV SIN vector genome into which was inserted a cassette containing (in order): Neo, an internal CMV promoter, truncated, codon-optimised human tyrosine hydroxylase (TH), EMCV internal ribosome entry site (IRES), codon-optimised human aromatic amino acid dopa decarboxylase (AADC), poliovirus IRES, GTP-cyclohydrolase I (GTP-CH1), and the woodchuck hepatitis virus post-transcriptional regulatory element (WPRE). The fusion plasmids containing two fused genes and one PV IRES element (FIG. 1: pONYK-ATiC, pONYK-TAiC, pONYK-TCiA, pONYK-CTiA and pONYK-AiTC) were generated by inserting regions of synthesised DNA (GeneArt, Germany) into the tricistronic cassette replacing the EMCV IRES region and the stop codon of the first gene with a GS15 linker. The GS15 linker codes for 4× glycine amino acids followed by 1× serine amino acid repeated in triplicate, which yields a linker of fifteen amino acids. The DNA sequence for this GS15 linker is as follows:

(SEQ ID NO. 3)
GGGGGAGGCGGTAGCGGCGGAGGGGGCTCCGGCGGAGGCGGGAGC.

When the triple fusion constructs (FIG. 1: pONYK-ATC and pONYK-TCA) were generated the PV IRES element was replaced with a second GS15 linker. The GS15 linker was also modified (GS15mod), in that the amino acid sequence remained unchanged while the DNA sequence differed. The new GS15mod linker DNA sequence is as follows:

(SEQ ID NO. 1)
GGAGGTGGCGGGTCCGGGGGCGGGGGTAGCGGTGGCGGGGGCTCC.

This GS15mod linker was cloned into the triple fusion constructs replacing one of the unmodified GS15 linkers (FIG. 1: pONYK-ATCmod and pONYK-TCAmod).

The VSV-G envelope and EIAV synthetic Gag/Pol plasmids used in this study were pHG and pESGPK, respectively.

Viral Vector Production

HEK293T cells were seeded into 10 cm dishes at a density of $3.5\times10^6$ cells/dish 24 h pre-transfection. Vector production was mediated by Lipofectamine™ 2000 CD (Invitrogen, Cat. 12566-101) according to the manufacturer's instructions. Briefly, the following quantities of plasmid were added to 340 μl OptiPRO™ (Gibco, Cat. 12309-019): 4 μg genome plasmid (see FIG. 1), 2 μg pESGPK and 0.08 μg pHG. This DNA mix was then added to a mix containing 25 μl Lipofectamine™ CD 2000 and 315 μl OptiPRO™. 14-18 h after transfection, sodium butyrate was added to a final concentration of 10 mM. Media was changed 6-8 h after sodium butyrate induction, and 21-23 h later vector was harvested and filtered through a 0.45 μm syringe filter. The vector titres, in transducing units/ml (TU/ml), were estimated by integration (DNA) titre assay.

Biochemical Assay

To test functionality of the catecholamine enzymes encoded by the different fusion constructs, a biochemical assay that measures the conversion of tyrosine to dopamine was performed using high-performance-liquid-chromatography (HPLC). To perform this assay, HEK293T cells were transduced with test vector and the PONYK1 control, in the presence of 10 μg $ml^{-1}$ polybrene (Sigma, cat. No. H9268). These cells were cultured for three days and then a tenth of the cells were used to seed cells for the catecholamine biochemical assay. The remaining cells were further passaged for analysis by integration (DNA) titre assay (see above). Two days later the media on the cells seeded for biochemical assay was replaced with media supplemented with L-Tyrosine (Sigma, Cat. No. T1145) at a final concentration of 100 mM, and the cells were cultured overnight. The following morning 800 μl of cell culture supernatant was harvested and placed into tubes containing a 80 μl of 2M Perchloric acid (Sigma, Cat. No. 244252) and 80 μl of Sodium Metabisulphite (Sigma, Cat. No. S9000). The samples were thoroughly mixed and once a precipitate had formed the samples were centrifuged at 10,000×g for 10 minutes to remove any debris. The supernatant was then removed to separate tubes and frozen in a −80° C. freezer until the HPLC analysis could be performed. The number of cells at the time of harvest was further ascertained.

Pre-HPLC analysis the samples were thawed and filtered through a 0.2 μM ultrapure PTFE filter (Millipore, Cat. No. UFC30LG25). The supernatants, alongside HPLC catecholamine standards, were applied to an HPLC system (Dionex) equipped with an ESA Coulochem II electrochemical detector (ESA Analytical). Catecholamines were separated using a C-18 reversed phase column (ESA Analytical) equilibriated with Cat-A-Phase (ESA Analytical) at a flow rate of 1.5 ml/min and then detected electrochemically. This HPLC assay is optimised for the detection of $_{L\text{-}DOPA}$, dihydroxyohenylacetic acid (DOPAC) and dopamine (DA) and results are expressed as the number of ng of $_{L\text{-}DOPA}$, DOPAC or DA per $10^5$ copies of integrated vector genome.

Detection of Catecholaminergic Enzymes by Western Blot Analysis

HEK293T cells that had been transiently transfected with the vector components were lysed in fractionation buffer (0.1M Tris.Cl, pH7.3, 0.2% (v/v) Nonidet P40 (BDS, cat. No. 56009). The total protein concentration was ascertained and 10 μg was loaded onto 4-20% polyacrylamide denaturing gels (Invitrogen, Cat. No. EC60285BOX). Western blotting was performed using one of the following: anti-CH1 antibody (obtained from Dr E. Werner, Austria), anti-TH antibody (Chemicon, Livingstone, UK, Cat. AB152) or anti-AADC antibody (Chemicon, Cat. AB136). Primary antibody incubation was followed by incubation with a peroxidase conjugated anti-rabbit secondary antibody (DAKO, Ely, UK, Cat. P0448). Visualisation was performed with ECL Advance Western Blotting Detection Kit (GE Healthcare UK Ltd, Little Chalfont, Cat. RPN2135).

Video Recording and Ethovision Analysis

Habituation to the video cage (no film required) is carried out over three sessions, each of 30 minutes. Baseline locomotor quantification is assessed by five 30-minute videos recorded in custom-made video cages using the Media Recorder acquisition software (Noldus). All videos are analysed using video tracking sotware, Ethovision (Noldus). Baseline locomotor activity of each animal consists of the mean locomotor activity calculated as the total distance travelled (TDT) on the last three videos acquired before MPTP intoxication begins. Challenge with oral L-DOPA is not performed at baseline prior to MPTP intoxication.

MPTP Intoxication

Animals (up to four at a time) are treated with a dose of 0.2 mg/kg MPTP for 7 days via intra muscular administration with at least a five-day break prior to initiation of a new MPTP cycle. MPTP cycles is repeated until locomotor activity has been reduced by between 80-90% of mean baseline activity and clinical scores are at least 8/14. A stable Parkinsonian behavioural score for at least three weeks is required before performing PET scans and/or treatment with viral vectors. The clinical scoring is adapted from Papa and Chase (Papa and Chase 1996 Ann. Neurol 39, 574-578) and is used to monitor MPTP-induced motor deficits on a daily basis upon initiation of MPTP intoxication and up to treatment with viral vectors. A thirty-minute video is acquired on a weekly basis starting three days after the last MPTP injection in order to quantify locomotor activity. Once animals are assessed to be stably Parkinsonian for three weeks (TDT variation ≤15%) an L-DOPA challenge and a separate negative control challenge as required are performed and animals are filmed for six hours for Ethovision analysis in order to determine the best 30-minute ON period to be compared with a 30-minute video of OFF time.

Animals are nursed and nutrition complemented by gavage (per os) if weight loss exceeds 12%.

Imaging Studies

MRI: Stereotactic MRI using 3D T2-weighted images are acquired before surgery in order to establish injection coordinates. All images are acquired on a 7 Tesla horizontal system (Varian-Agilent Technologies, USA) equipped with a gradient coil reaching 100 mT/m (300 s rise time) and a circular radiofrequency 1H coil (12 cm inner diameter).

PET: $^{18}$F-FMT and $^{18}$F-Fallypride scans are performed on all animals once they are assessed to be stably Parkinsonian as described above. Initially four healthy control animals are imaged with both $^{18}$F-FMT and $^{18}$F-Fallypride to establish the quantification method that is applied throughout the study. Scans are performed under propofol anaesthetic using a FOCUS 220 PET scanner (Siemens) with a 1.5 mm axial resolution and a 4% sensitivity. Animals are imaged in pairs on different days to allow radioactive decay between the different tracers.

Surgery

Vectors are injected into the putamen of each hemisphere (as calculated from a m. *fascicularis* brain atlas). For each hemisphere, the first injection of 50 L is 1 mm caudal from the anterior commissure. The second injection of 50 L is 4 mm caudal from the anterior commissure. The injections of 2×50 μL depositis/hemisphere are made at a flow rate of 3 L/min under propofol anesthesia using a 28 gauge 51 mm length blunt stainless steel needle attached to a 100 μL Hamilton glass syringe. Guide tubes are also used to ensure correct positioning of the vector deposit.

Post-Treatment Behavioural Follow-Up

Nursing continues as necessary.

A 30-minute video recording is taken every week starting 3 weeks post-surgery and ending 3 months post-surgery.

Between 3 and 6 months post-surgery a 30 minute video recording is taken every two weeks. Clinical scoring is performed weekly between 0 and 3 months post-surgery and every 2 weeks between 3 and 6 months post-surgery. The Clinical Rating Score assessment is described in Jarraya et al 2009, Science Translational Medicine 1:2ra4.

An MRI scan, $^{18}$F-FMT and $^{18}$F-Fallypride PET scans are all performed at 3 months post-surgery. L-DOPA challenge is also performed at 3 months post surgery and animals are filmed for 6 hours for Ethovision analysis. A negative control challenge is also performed as required followed by Ethovision analysis.

Post Mortem Analysis

Following euthanasia brains are removed and processed prior to staining with antibodies and βgal.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, virology, neurobiology or related fields are intended to be within the scope of the following claims.

The invention claimed is:

1. A method for producing dopamine in a subject having Parkinson's disease, the method comprising directly injecting or infusing to the putamen of the subject, an effective amount of equine infectious anemia virus (EIAV) vector comprising a nucleic acid construct comprising:

(i) a nucleotide sequence which encodes tyrosine hydroxylase (TH), (ii) a nucleotide sequence which encodes GTP-cyclohydrolase I (CH1), and (iii) a nucleotide sequence which encodes Aromatic Amino Acid Dopa Decarboxylase (AADC);

wherein the nucleotide sequence encoding TH 1s linked to the nucleotide sequence encoding CH1 such that they encode a fusion protein TH-CH1, wherein the construct comprises TH-$_L$-CH1-$_{IRE}$s-AADC, wherein L is a linker-encoding sequence, and IRES is an Internal Ribosome Entry Site, thereby producing dopamine in the subject.

2. The method according to claim 1, wherein the linker is not codon optimized for human usage.

3. The method according to claim 1, wherein the linker comprises the nucleic acid sequence as set forth in SEQ ID No. 1.

4. The method according to claim 1, wherein the EIAV vector is pseudotyped with VSV-G.

* * * * *